United States Patent
Haddad et al.

(10) Patent No.: US 11,679,268 B2
(45) Date of Patent: Jun. 20, 2023

(54) MULTI-TIER PREDICTION OF CARDIAC TACHYARRYTHMIA

(71) Applicant: Medtronic, Inc., Minneapolis, MN (US)

(72) Inventors: Tarek D Haddad, Minneapolis, MN (US); Athula I Abeyratne, Maplewood, MN (US); Mark L. Brown, North Oaks, MN (US); Donald R Musgrove, Minneapolis, MN (US); Andrew Radtke, Minneapolis, MN (US); Mugdha V Tasgaonkar, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 498 days.

(21) Appl. No.: 16/593,739

(22) Filed: Oct. 4, 2019

(65) Prior Publication Data
US 2020/0108260 A1 Apr. 9, 2020

Related U.S. Application Data

(60) Provisional application No. 62/741,736, filed on Oct. 5, 2018.

(51) Int. Cl.
*A61N 1/39* (2006.01)
*A61B 5/00* (2006.01)
(Continued)

(52) U.S. Cl.
CPC ............ *A61N 1/3956* (2013.01); *A61B 5/363* (2021.01); *A61B 5/7264* (2013.01);
(Continued)

(58) Field of Classification Search
CPC ....... A61B 5/021; A61B 5/024; A61B 5/1118; A61B 5/355; A61B 5/4809; A61B 5/4818;
(Continued)

(56) References Cited

U.S. PATENT DOCUMENTS 4,458,691 A  7/1984 Netravali
6,212,428 B1 4/2001 Hsu et al.
(Continued)

FOREIGN PATENT DOCUMENTS

CN 108030488 A 5/2018
EP  1218060 B1 8/2004
(Continued)

OTHER PUBLICATIONS

Isin et al., "Cardiac Arrhythmia Detection Using Deep Learning," Procedia Computer Science vol. 120, 2017 (Applicant points out, in accordance with MPEP 609.04(a), that the year of publication, 2017, is sufficiently earlier than the effective U.S. filing date, so that the particular month of publication is not in issue.) pp. 268-275.
(Continued)

*Primary Examiner* — Mallika D Fairchild
*Assistant Examiner* — Shreya Anjaria
(74) *Attorney, Agent, or Firm* — Shumaker & Sieffert, P.A.

(57) ABSTRACT

Techniques are disclosed for a multi-tier system for predicting cardiac arrhythmia in a patient. In one example, a computing device processes parametric patient data and provider data for a patient to generate a long-term probability that a cardiac arrhythmia will occur in the patient within a first time period. In response to determining that the cardiac arrhythmia is likely to occur within the first time period, the computing device causes a medical device to process the parametric patient data to generate a short-term
(Continued)

probability that the cardiac arrhythmia will occur in the patient within a second time period. In response to determining that the cardiac arrhythmia is likely to occur within the second time period, the medical device performs a remediative action to reduce the likelihood that the cardiac arrhythmia will occur.

17 Claims, 12 Drawing Sheets

(51) Int. Cl.
*A61B 5/363* (2021.01)
*A61N 1/37* (2006.01)
*G16H 10/60* (2018.01)
*G16H 50/30* (2018.01)
*G16H 50/20* (2018.01)
*G06N 20/00* (2019.01)
*G06N 3/02* (2006.01)

(52) U.S. Cl.
CPC .......... *A61B 5/7275* (2013.01); *A61B 5/7282* (2013.01); *A61N 1/3706* (2013.01); *G06N 3/02* (2013.01); *G06N 20/00* (2019.01); *G16H 10/60* (2018.01); *G16H 50/20* (2018.01); *G16H 50/30* (2018.01)

(58) Field of Classification Search
CPC ... A61B 5/4836; A61B 5/7264; A61B 5/7267; A61B 5/7275; A61B 5/7282; A61N 1/3706; A61N 1/37211; A61N 1/3925; A61N 1/395; A61N 1/3956; A61N 1/3962; A61N 1/3987; G06N 3/02; G06N 3/0427; G06N 3/08; G06N 20/00; G06N 3/042; G06N 3/045; G16H 10/60; G16H 20/30; G16H 40/63; G16H 50/20; G16H 50/30
See application file for complete search history.

(56) References Cited

U.S. PATENT DOCUMENTS

| | | | |
|---|---|---|---|
| 6,308,094 | B1 | 10/2001 | Shusterman et al. |
| 6,594,523 | B1 | 7/2003 | Levine |
| 8,103,346 | B2 | 1/2012 | Mass et al. |
| 8,521,281 | B2 | 8/2013 | Patel et al. |
| 9,183,351 | B2 | 11/2015 | Shusterman |
| 9,483,529 | B1 | 11/2016 | Pasoi et al. |
| 9,585,590 | B2 | 3/2017 | McNair |
| 9,743,890 | B2 | 8/2017 | Lord et al. |
| 9,775,559 | B2 | 10/2017 | Zhang et al. |
| 10,463,269 | B2 | 11/2019 | Boleyn et al. |
| 10,744,334 | B2 | 8/2020 | Perschbacher et al. |
| 2002/0016550 | A1* | 2/2002 | Sweeney ................. G16Z 99/00 600/515 |
| 2002/0123768 | A1 | 9/2002 | Gilkerson et al. |
| 2006/0247709 | A1* | 11/2006 | Gottesman ......... A61N 1/37282 607/30 |
| 2009/0259269 | A1 | 10/2009 | Brown |
| 2010/0179444 | A1 | 7/2010 | O'Brien et al. |
| 2010/0268103 | A1 | 10/2010 | McNamara et al. |
| 2010/0280841 | A1 | 11/2010 | Dong et al. |
| 2011/0270109 | A1 | 11/2011 | Zhang et al. |
| 2012/0004563 | A1 | 1/2012 | Kim et al. |
| 2012/0209126 | A1 | 8/2012 | Amos et al. |
| 2013/0274524 | A1 | 10/2013 | Dakka et al. |
| 2013/0274624 | A1 | 10/2013 | Mahanjan et al. |
| 2014/0257063 | A1 | 9/2014 | Ong et al. |
| 2014/0378856 | A1 | 12/2014 | Koike et al. |
| 2015/0164349 | A1 | 6/2015 | Gopalakrishnan et al. |
| 2015/0216435 | A1 | 8/2015 | Bokan et al. |
| 2015/0265217 | A1 | 9/2015 | Penders et al. |
| 2016/0022164 | A1 | 1/2016 | Brockway et al. |
| 2016/0135706 | A1* | 5/2016 | Sullivan ................. A61B 5/316 600/509 |
| 2016/0192853 | A1 | 7/2016 | Bardy et al. |
| 2016/0220137 | A1 | 8/2016 | Mahajan et al. |
| 2016/0232280 | A1 | 8/2016 | Apte et al. |
| 2017/0095673 | A1 | 4/2017 | Ludwig et al. |
| 2017/0105683 | A1 | 4/2017 | Xue |
| 2017/0156592 | A1 | 6/2017 | Fu |
| 2017/0196458 | A1 | 7/2017 | Ternes et al. |
| 2017/0265765 | A1 | 9/2017 | Baumann et al. |
| 2017/0290550 | A1 | 10/2017 | Perschbacher et al. |
| 2017/0347894 | A1 | 12/2017 | Bhushan et al. |
| 2017/0354365 | A1 | 12/2017 | Zhou |
| 2018/0008976 | A1 | 3/2018 | Okazaki |
| 2018/0089763 | A1 | 3/2018 | Okazaki |
| 2018/0146874 | A1 | 5/2018 | Walker et al. |
| 2018/0146929 | A1 | 5/2018 | Joo et al. |
| 2018/0206721 | A1 | 7/2018 | Zhang |
| 2018/0233227 | A1 | 8/2018 | Galloway et al. |
| 2018/0272147 | A1 | 9/2018 | Freeman et al. |
| 2018/0279891 | A1 | 10/2018 | Miao et al. |
| 2018/0310892 | A1 | 11/2018 | Perschbacher et al. |
| 2019/0008461 | A1 | 1/2019 | Gupta et al. |
| 2019/0029552 | A1 | 1/2019 | Perschbacher et al. |
| 2019/0038148 | A1 | 2/2019 | Valys et al. |
| 2019/0038149 | A1 | 2/2019 | Gopalakrishnan et al. |
| 2019/0090774 | A1 | 3/2019 | Yang et al. |
| 2019/0122097 | A1 | 4/2019 | Shibahara et al. |
| 2019/0209022 | A1 | 7/2019 | Sobol et al. |
| 2019/0272920 | A1 | 9/2019 | Teplitzky |
| 2019/0275335 | A1 | 9/2019 | Volpe et al. |
| 2019/0328251 | A1 | 10/2019 | Jin |
| 2019/0343415 | A1 | 11/2019 | Saha et al. |
| 2019/0365342 | A1 | 12/2019 | Ghaffarzadegan et al. |
| 2019/0378620 | A1 | 12/2019 | Saren |
| 2020/0100693 | A1 | 4/2020 | Velo |
| 2020/0108260 | A1 | 4/2020 | Haddad et al. |
| 2020/0178825 | A1 | 6/2020 | Weijia et al. |
| 2020/0288997 | A1 | 9/2020 | Shute et al. |
| 2020/0352462 | A1 | 11/2020 | Pedalty et al. |
| 2020/0352466 | A1 | 11/2020 | Chakravarthy et al. |
| 2020/0352521 | A1 | 11/2020 | Chakravarthy et al. |
| 2020/0353271 | A1 | 11/2020 | Dani et al. |
| 2020/0357517 | A1 | 11/2020 | Haddad et al. |
| 2020/0357518 | A1 | 11/2020 | Musgrove et al. |
| 2020/0357519 | A1 | 11/2020 | Chakravarthy et al. |
| 2021/0137384 | A1 | 5/2021 | Robinson et al. |
| 2021/0169736 | A1 | 6/2021 | Wijshoff et al. |
| 2021/0204858 | A1 | 7/2021 | Attia et al. |
| 2021/0338134 | A1 | 11/2021 | Chakravarthy et al. |
| 2021/0338138 | A1 | 11/2021 | Pedalty et al. |
| 2021/0343416 | A1 | 11/2021 | Chakravarthy et al. |
| 2021/0345865 | A1 | 11/2021 | Spillinger et al. |
| 2021/0358631 | A1 | 11/2021 | Haddad et al. |

FOREIGN PATENT DOCUMENTS

| | | |
|---|---|---|
| EP | 2427105 A1 | 3/2012 |
| WO | 2010129447 A1 | 11/2010 |
| WO | 2013/160538 A1 | 10/2013 |
| WO | 2017072250 A1 | 5/2017 |
| WO | 2017091736 A1 | 6/2017 |
| WO | 2018119316 A1 | 6/2018 |
| WO | 2020049267 A1 | 3/2020 |

OTHER PUBLICATIONS

Swerdlow et al., "Troubleshooting Implanted Cardioverter Defibrillator Sensing Problems I," Advances in Arrhythmia and Electrophysiology, vol. 7, No. 6, Dec. 2014, pp. 1237-1261.

Wartzek et al., "ECG on the Road: Robust and Unobtrusive Estimation of Heart Rate," IEEE Transactions on Biomedical Engineering, vol. 58, No. 11, Nov. 2011, pp. 3112-3120.

Anonymous, "Receiver Operating Characteristic—Wikipedia," Mar. 20, 2019, Retrieved from the Internet: URL: https://en.wikipedia.org/w/index.php?title=Receiver_operating_characteristic&oldis=888671034#History, 12 pp.

(56) References Cited

OTHER PUBLICATIONS

Habibzadeh et al., "On determining the most appropriate test cut-off value: the case of tests with continuous results," Biochemia Medica, Oct. 15, 2016, pp. 297-307.
U.S. Appl. No. 17/373,480, filed Jul. 12, 2021, naming inventors Chakravarthy et al.
U.S. Appl. No. 17/377,763, filed Jul. 16, 2021, naming inventors Chakravarthy et al.
U.S. Appl. No. 17/377,785, filed Jul. 16, 2021, naming inventors Pedalty et al.
U.S. Appl. No. 17/383,170, filed Jul. 22, 2021, naming inventors Haddad et al.
International Preliminary Report on Patentability from International Application No. PCT/US2019/054841, dated Apr. 15, 2021, 10 pp.
PCT Search Report dated Jun. 25, 2020, corresponding to counterpart PCT Application No. PCT/US2019/054841; 5 pages.
Kelwade et al., "Prediction of Cardiac Arrhythmia using Artificial Neural Network," International Journal of Computer Applications (0975-8887), vol. 115—No. 20, Apr. 2015, 6 pp.
Lau et al., "Connecting the Dots: From Big Data to Healthy Heart," HHS Public Access Author manuscript, Aug. 2, 2017, 5 pp.
Schwab et al., "Beat by Beat: Classifying Cardiac Arrhythmias with Recurrent Neural Networks," Mobile Health Systems Lab, Department of Health Sciences and Technology, Oct. 24, 2017, 4 pp.
U.S. Appl. No. 62/843,738, filed May 6, 2019 by Chakravarthy et al.
U.S. Appl. No. 62/843,717, filed May 6, 2019 by Chakravarthy et al.
U.S. Appl. No. 62/843,730, filed May 6, 2019 by Pedalty et al.
"Visualize Features of a Convolutional Neural Network," MATLAB & Simulink, retrieved from https://www.mathworks.com/help/deeplearning/examples/visualize-features-of-a-convolutional-neural-network.html, Sep. 11, 2019, 7 pp.
Invitation to Pay Additional Fees from International Application No. PCT/US2019/054841, dated Feb. 28, 2020, 11 pp.
Fawaz et al., "Deep learning for time series classification: a review," Irimas, Universite Haute Alsace, Dec. 7, 2018, 53 pp.
Classify ECG Signals Using Long Short-Term Memory Networks, MATLAB, retrieved from https://www.mathworks.com/help/signal/examples/classify-ecg-signals-using-long-short-term-memory-networks.html, Nov. 2, 2018, 19 pp.
"Visualize Features of a Convolutional Neural Network," MATLAB & Simulink, Mar. 15, 2018, 9 pp.
U.S. Appl. No. 62/843,707, filed May 6, 2019 by Dani et al.
U.S. Appl. No. 62/843,702, filed May 6, 2019 by Musgrove et al.
U.S. Appl. No. 62/843,762, filed May 6, 2019 by Chakravarthy et al.
U.S. Appl. No. 62/843,786, filed May 6, 2019 by Haddad et al.
U.S. Appl. No. 16/845,996, filed Apr. 10, 2020 by Haddad et al.
U.S. Appl. No. 16/851,603, filed Apr. 17, 2020 by Chakravarthy et al.
Schirrmeister et al., "Deep learning with convolutional neural networks for brain mapping and decoding of movement-related information from the human EEG," arXiv:170.05051v1, Mar. 16, 2017, 58 pp.
U.S. Appl. No. 16/832,732, filed Mar. 27, 2020 by Chakravarthy et al.
U.S. Appl. No. 16/850,833, filed Apr. 16, 2020 by Dani et al.
U.S. Appl. No. 16/851,500, filed Apr. 17, 2020 by Musgrove et al.
U.S. Appl. No. 16/850,699, filed Apr. 16, 2020, by Chakravarthy et al.
U.S. Appl. No. 16/850,749, filed Apr. 16, 2020, by Pedalty et al.
Witten et al., "Data mining: Practical Machine Learning Tools and Techniques," Third Edition, Morgan Kaufmann, Feb. 3, 2011, 665 pp.
Bresnick, "Machine Learning Algorithm Outperforms Cardiologists Reading EKGs", Health IT Analytics, Jul. 12, 2017, 5 pages.
Chen et al., "Electrocardiogram Recognition Based on Variational AutoEncoder," Machine Learning and Biometrics, IntechOpen, Aug. 29, 2018, pp. 71-90.
Andersen et al., "A Deep Learning Approach for Real-Time Detection of Atrial Fibrillation," Expert Systems with Applications, vol. 114, Aug. 14, 2018, pp. 465-473.
Arrobo et al., "An Innovative Wireless Cardiac Rhythm Management (iCRM) System," Computer Science, 2014 Wireless Telecommunications Symposium, Jun. 2014, 5 pp.
Madani et al., "Fast and Accurate View Classification of Echocardiograms Using Deep Learning," Nature Partner Journals, vol. 1, No. 6, Mar. 21, 2018, 8 pp.
Schirrmeister et al., "Deep Learning with Convolutional Neural Networks for Brain Mapping and Decoding of Movement-Related Information from the Human EEG," Cornell University Library, Mar. 16, 2017, 58 pp.

\* cited by examiner

MULTI-TIER PREDICTION OF CARDIAC TACHYARRYTHMIA

This application claims the benefit of U.S. Provisional Patent Application No. 62/741,736, filed Oct. 5, 2018, the entire content of which is incorporated by reference herein.

FIELD

This disclosure generally relates to medical devices and, more particularly, to implantable medical devices.

BACKGROUND

Malignant tachyarrhythmia, for example, ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. Consequently, sudden cardiac death (SCD) may result in a matter of minutes.

In patients with a high risk of ventricular fibrillation, the use of an implantable medical device (IMD), such as an implantable cardioverter defibrillator (ICD), has been shown to be beneficial at preventing SCD. An ICD is a battery powered electrical shock device, that may include an electrical housing electrode (sometimes referred to as a can electrode), that is typically coupled to one or more electrical lead wires placed within the heart. If an arrhythmia is sensed, the ICD may send a pulse via the electrical lead wires to shock the heart and restore its normal rhythm. Some ICDs have been configured to attempt to terminate detected tachyarrhythmias by delivery of anti-tachycardia pacing (ATP) prior to delivery of a shock. Additionally, ICDs have been configured to deliver relatively high magnitude post-shock pacing after successful termination of a tachyarrhythmia with a shock, in order to support the heart as it recovers from the shock. Some ICDs also deliver bradycardia pacing, cardiac resynchronization therapy (CRT), or other forms of pacing.

SUMMARY

In general, the disclosure describes techniques for multi-tier prediction of cardiac arrhythmia in a patient. In some examples, a multi-tier system implements the techniques. In one example, a computing device receives parametric patient data collected by one or more electrodes and/or sensors of a medical device of the patient. The computing device may further receive provider data for the patient from a database. In some examples, the computing device is a cloud computing system. The computing device applies a machine learning model, trained using parametric patient data and provider data for a plurality of patients, to the parametric patient data and the provider data for the patient to generate a long-term probability that a cardiac arrhythmia will occur in the patient within a first time period (e.g., typically about 24 hours to about 48 hours). The computing device determines whether the long-term probability exceeds a long-term predetermined threshold, and, in response to determining that the long-term probability exceeds the long-term predetermined threshold, transmits instructions to the medical device causing the medical device to determine a short-term probability that the cardiac arrhythmia will occur in the patient within a second time period (e.g., shorter than the first period of time, and typically about 30 minutes to about 60 minutes). In some examples, the long-term predetermined threshold is 50%.

In response to receiving the instructions from the computing device, the medical device processes subsequent parametric patient data to generate the short-term probability that the cardiac arrhythmia will occur in the patient within the second time period. In response to determining that the short-term probability exceeds a short-term predetermined threshold, the medical device performs a remediative action to reduce the short-term probability that the cardiac arrhythmia will occur in the patient within the second time period. For example, the medical device may issue a notification of the short-term probability that the cardiac arrhythmia will occur in the patient within the second time period to a computing device such that the patient or a clinician may become aware of the likelihood the cardiac arrhythmia will occur in the patient within the second time period. In another example, the medical device (or another medical device local to the patient and in communication with the medical device that determines the short-term probability) initiates drug delivery therapy or electrical pacing therapy to reduce the likelihood the cardiac arrhythmia will occur in the patient within the second time period. In some examples, the short-term predetermined threshold is 95%.

As an example of the foregoing, the computing device, in response to determining that there is greater than a 50% likelihood that a cardiac arrhythmia will occur in the patient within the next 24 hours, transmits instructions to the medical device causing the medical device to determine the short-term probability. The medical device, in response to determining that there is greater than a 95% likelihood that a cardiac arrhythmia will occur in the patient within the next 60 minutes, performs a remediative action to reduce likelihood that a cardiac arrhythmia will occur in the patient within the next 60 minutes.

Thus, the techniques disclosed herein may allow for enhanced patient care and increase the ability to prevent cardiac arrhythmias in a patient. For example, the knowledge that tachyarrhythmia has a relatively high likelihood of occurring within the next few days may be used to help guide preventative care for the patient. Further, the knowledge that tachyarrhythmia has a relatively high likelihood of occurring within the next few minutes or hours may be used to guide preventative therapies or emergency care for the patient. Furthermore, such a system as disclosed herein may move long-term cardiac arrhythmia prediction operations that are computationally-expensive and power consuming from a personal medical device of a patient to a cloud computing system, and activate short-term cardiac prediction operations on the medical device only when the cloud computing system predicts that a cardiac arrhythmia has a relatively high likelihood of occurring within the next few days. Thus, the techniques of the disclosure may conserve power and extend battery life of a medical device by using the medical device for cardiac prediction only when a cardiac arrhythmia has a relatively high likelihood of occurring within a particular time span.

In one example, this disclosure describes a computing device comprising processing circuitry and a storage medium, the computing device configured to: receive parametric patient data for a patient; apply a machine learning model, trained using parametric patient data for a plurality of patients, to the parametric patient data to generate a first probability that a cardiac arrhythmia will occur in the patient within a first time period; determine that the first probability exceeds a predetermined threshold; and in response to the determination that the first probability exceeds the predetermined threshold, transmit instructions to a second device causing the second device to determine a second probability that a cardiac arrhythmia will occur in the patient within a second time period.

In another example, this disclosure describes a device configured to: collect, via one or more of a plurality of electrodes or sensors, parametric patient data for a patient; receive instructions from a computing device to generate a probability that a cardiac arrhythmia will occur in the patient within a time period; in response to the instructions, process the parametric patient data to generate the probability that the cardiac arrhythmia will occur in the patient within the time period; determine that the probability exceeds a predetermined threshold; and in response to the determination that the probability exceeds the predetermined threshold, perform a remediative action to reduce the probability that the cardiac arrhythmia will occur in the patient within the time period.

In another example, this disclosure describes an external device configured to: receive instructions to generate a first probability that a cardiac arrhythmia will occur in the patient within a first time period; in response to the instructions, process parametric patient data to generate the first probability that the cardiac arrhythmia will occur in the patient within the first time period; determine that the first probability exceeds a first predetermined threshold; and in response to the determination that the first probability exceeds the first predetermined threshold, transmit instructions to a medical device causing the medical device to determine a second probability that a cardiac arrhythmia will occur in the patient within a second time period.

In another example, this disclosure describes a method comprising: receiving, by a computing device comprising processing circuitry and a storage medium, parametric patient data for a patient; applying, by the computing device, a machine learning model, trained using parametric patient data for a plurality of patients, to the parametric patient data to generate a first probability that a cardiac arrhythmia will occur in the patient within a first time period; determining, by the computing device, that the first probability exceeds a predetermined threshold; and in response to the determination that the first probability exceeds the predetermined threshold, transmitting, by the computing device, instructions to a second device causing the second device to determine a second probability that a cardiac arrhythmia will occur in the patient within a second time period.

In another example, this disclosure describes a method comprising: collecting, by a device, parametric patient data for a patient; receiving, by the device, instructions from a computing device to generate a probability that a cardiac arrhythmia will occur in the patient within a time period; in response to the instructions, processing, by the device, the parametric patient data to generate the probability that the cardiac arrhythmia will occur in the patient within the time period; determining, by the device, that the probability exceeds a predetermined threshold; and in response to the determination that the probability exceeds the predetermined threshold, performing, by the device, a remediative action to reduce the probability that the cardiac arrhythmia will occur in the patient within the time period.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

Like reference characters refer to like elements throughout the figures and description.

DETAILED DESCRIPTION

Figure 1:
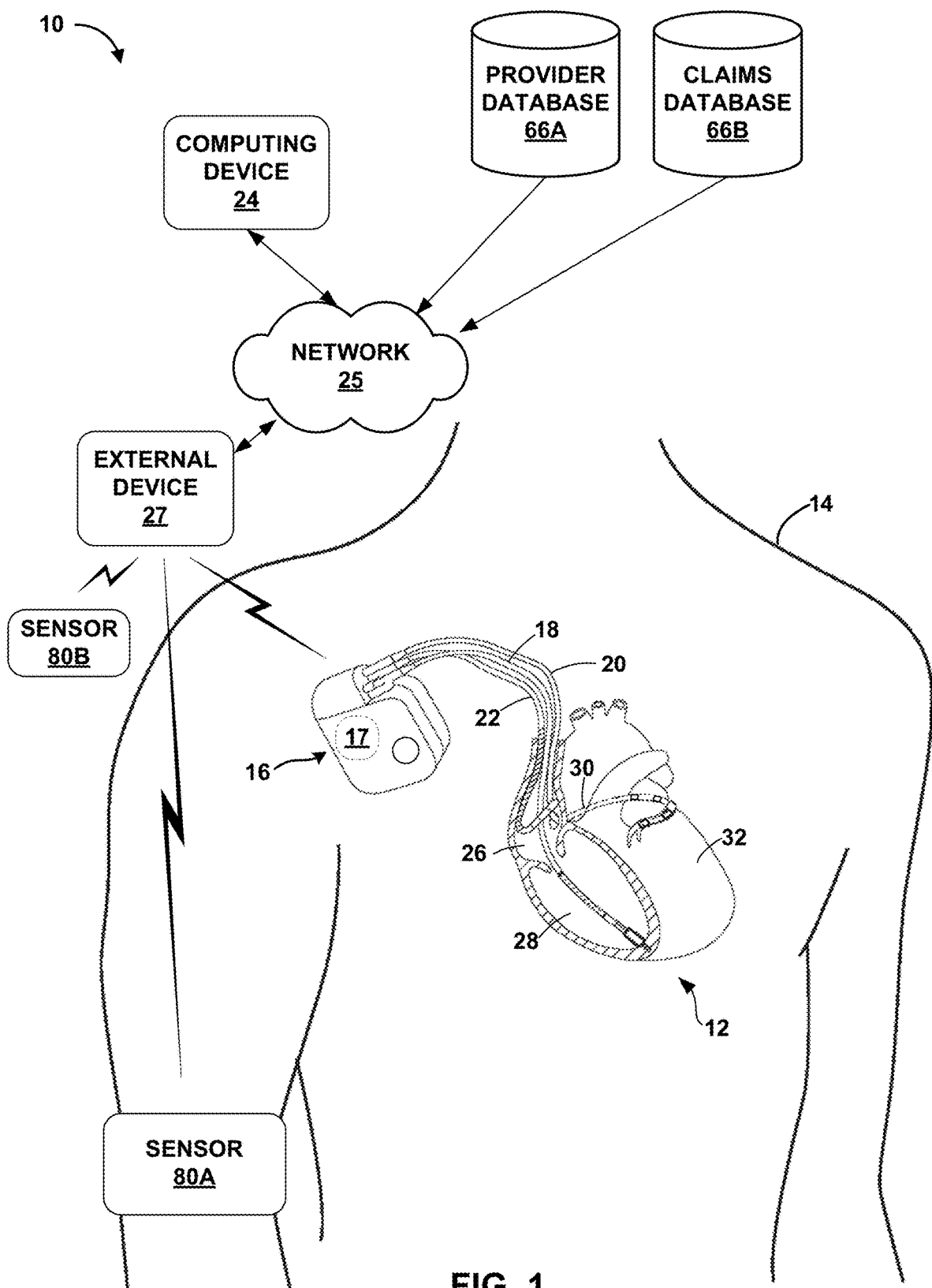
FIG. 1 is a block diagram illustrating an example system for predicting cardiac arrhythmia in accordance with the techniques of the disclosure.

FIG. 1 is a block diagram illustrating an example system for predicting cardiac arrhythmia in accordance with the techniques of the disclosure. System 10 includes a medical device. One example of such a medical device is IMD 16 depicted in FIG. 1. As illustrated by example system 10 in FIG. 1, IMD 16 may, in some examples, be an implantable cardiac pacemaker, implantable cardioverter/defibrillator (ICD), or pacemaker/cardioverter/defibrillator, for example. IMD 16 is connected to leads 18, 20 and 22 and is communicatively coupled to external device 27, which in turn is communicatively coupled to computing device 24 over communication network 25.

IMD 16 senses electrical signals attendant to the depolarization and repolarization of heart 12, e.g., a cardiac electrogram (EGM), via electrodes on one or more leads 18, 20 and 22 or the housing of IMD 16. IMD 16 may also deliver therapy in the form of electrical signals to heart 12 via electrodes located on one or more leads 18, 20 and 22 or a housing of IMD 16. The therapy may be pacing, cardioversion and/or defibrillation pulses. IMD 16 may monitor EGM signals collected by electrodes on leads 18, 20 or 22, and based on the EGM signal, diagnose, and treat cardiac episodes.

In some examples, IMD 16 includes communication circuitry 17 including any suitable circuitry, firmware, software, or any combination thereof for communicating with another device, such as external device 27 of FIG. 1. For example, communication circuitry 17 may include one or more processors, memory, wireless radios, antennae, transmitters, receivers, modulation and demodulation circuitry, filters, amplifiers, or the like for radio frequency communication with other devices, such as computing device 24. IMD 16 may use communication circuitry 17 to receive downlinked data from to control one or more operations of IMD 16 and/or send uplinked data to external device 27.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

While example system 10 of FIG. 1 depicts IMD 16, in other examples, the techniques of the disclosure may be applied to other types of medical devices that are not necessarily implantable. For example, a medical device in accordance with the techniques of the disclosure may include a wearable medical device or "smart" apparel worn by patient 14. For example, such a medical device may take the form of a wristwatch worn by patient 14 or circuitry that is adhesively affixed to patient 14. In another example, a medical device as described herein may include an external medical device with implantable electrodes.

In some examples, external device 27 takes the form of an external programmer or mobile device, such as a mobile phone, a "smart" phone, a laptop, a tablet computer, a personal digital assistant (PDA), a wearable electronic device, etc. In some examples, external device 27 is a CareLink™ monitor available from Medtronic, Inc. A user, such as a physician, technician, surgeon, electro-physiologist, or other clinician, may interact with external device 27 to retrieve physiological or diagnostic information from IMD 16. A user, such as patient 14 or a clinician as described above, may also interact with external device 27 to program IMD 16, e.g., select or adjust values for operational parameters of IMD 16. External device 27 may include processing circuitry, a memory, a user interface, and communication circuitry capable of transmitting and receiving information to and from each of IMD 16 and computing device 24.

In some examples, computing device 24 takes the form of a handheld computing device, computer workstation, server or other networked computing device, smartphone, tablet, or external programmer that includes a user interface for presenting information to and receiving input from a user. In some examples, computing device 24 may include one or more devices that implement a machine learning system, such as a neural network, a deep learning system, or other type of predictive analytics system. A user, such as a physician, technician, surgeon, electro-physiologist, or other clinician, may interact with computing device 24 to retrieve physiological or diagnostic information from IMD 16. A user may also interact with computing device 24 to program IMD 16, e.g., select values for operational parameters of the IMD. Computing device 24 may include a processor configured to evaluate EGM and/or other sensed signals transmitted from IMD 16 to computing device 24.

Network 25 may include one or more computing devices (not shown), such as one or more non-edge switches, routers, hubs, gateways, security devices such as firewalls, intrusion detection, and/or intrusion prevention devices, servers, computer terminals, laptops, printers, databases, wireless mobile devices such as cellular phones or personal digital assistants, wireless access points, bridges, cable modems, application accelerators, or other network devices. Network 25 may include one or more networks administered by service providers, and may thus form part of a large-scale public network infrastructure, e.g., the Internet. Network 25 may provide computing devices, such as computing device 24 and IMD 16, access to the Internet, and may provide a communication framework that allows the computing devices to communicate with one another. In some examples, network 25 may be a private network that provides a communication framework that allows computing device 24, IMD 16, provider database 66, and claims database 68 to communicate with one another but isolates computing device 24, IMD 16, provider database 66, and claims database 68 from external devices for security purposes. In some examples, the communications between computing device 24, IMD 16, provider database 66, and claims database 68 are encrypted.

External device 27 and computing device 24 may communicate via wireless communication over network 25 using any techniques known in the art. In some examples, computing device 24 is a remote device that communicates with external device 27 via an intermediary device located in network 25, such as a local access point, wireless router, or gateway. While in the example of FIG. 1, external device 27 and computing device 24 communicate over network 25, in some examples, external device 27 and computing device 24 communicate with one another directly. Examples of communication techniques may include, for example, communication according to the Bluetooth® or Bluetooth® Low Energy (BLE) protocols. Other communication techniques are also contemplated. Computing device 24 may also communicate with one or more other external devices using a number of known communication techniques, both wired and wireless.

Provider database 66 stores provider data for patient 14. Claims database 68 may store claims or payor information for patient 14, such as health records stored by an insurance provider or other payor for patient 14. Provider database 66 and claims database 68 may include processing circuitry and one or more storage mediums (e.g., random access memory (RAM), read only memory (ROM), programmable read only memory (PROM), erasable programmable read only memory (EPROM), electronically erasable programmable read only memory (EEPROM), or flash memory. In some examples, provider database 66 is a cloud computing system. In some examples, the functions of provider database 66 are distributed across a number of computing systems.

In accordance with the techniques of the disclosure, system 10 provides multi-tier prediction of cardiac arrhythmia in a patient. In some examples, system 10 provides long-term and short-term prediction of cardiac ventricular arrhythmias. In some examples, the long-term time period is about 24 hours to about 48 hours. In some examples, the short-term time period is about 30 minutes to about 60 minutes. In some examples, the long-term time period is greater than about 1 day and less than about 1 week and the short-term time period is greater than about 1 minute and less than about 1 day. In some examples, the long-term time period is less than about 1 day and the short-term time period is less than about 1 hour.

In one example, computing device 24 receives parametric patient data collected by a medical device of patient 14. In some examples, the parametric patient data includes physiological data for patient 14, such as one or more of an activity level of patient 14, a heart rate of patient 14, a posture of patient 14, a cardiac electrogram of patient 14, a blood pressure of patient 14, a pulse transit time of patient 14, a respiration rate of patient 14, a hypopnea index or apnea of patient 14, accelerometer data for patient 14, features derived from accelerometer data of patient 14, such as activity counts, posture, statistical control process variables, etc., a raw electromyogram of patient 14, one or more features derived from a raw electromyogram of patient 14, such as heart rate variability, t-wave alternans, QRS morphology, etc., interval data and features derived from interval data, heart sounds, potassium levels, glycemic index, a temperature of patient 14, or any data derivable from the aforementioned parametric data, or any other types of parametric patient data. In some examples, the parametric patient data includes behavioral data or demographic data for patient 14, such as an age of patient 14, a gender of patient 14, activity patterns of patient 14, sleep patterns of patient 14, gait changes of patient 14, or temperature trends of the medical device or patient 14. In some examples, the medical device may automatically generate the parametric patient data by processing information from one or more sensors. For example, the medical device may determine, via one or more sensors, that patient 14 has fallen down, patient 14 is frail or suffers an illness, or that patient 14 is suffering an instance of sleep apnea.

In some examples, the parametric patient data includes environmental data such as, air quality measurements, ozone levels, particulate counts, or pollution levels proximate to patient 14, an ambient temperature, or daylight hours. In some examples, one of the medical device, sensors 80 or external device 27 may sense, via one or more sensors, the environmental data. In another example, the environmental data is received by external device 27 via an application, such as a weather application, executing on external device 27, and uploaded to computing device 24 over network 25. In another example, computing device 24 collects the environmental data directly from a cloud service that has location-based data for patient 14.

In some examples, the parametric patient data includes patient symptom data that is uploaded by patient 14 via an external device, such as external device 27. For example, patient 14 may upload the patient symptom data via an application executing on a smart phone. In some examples, patient 14 may upload the upload the patient symptom data via a user interface (not depicted in FIG. 1), such as by touchscreen, keyboard, graphical user interface, voice commands, etc. In other examples, an image of the patient may be obtained via a camera of external device 27 and process the image of the patient to identify patient symptom data.

In some examples, the parametric patient data includes device-related data, such as one or more of an impedance of one or more electrodes of the medical device, a selection of electrodes, a drug delivery schedule for the medical device, a history of electrical pacing therapy delivered to the patient, diagnostic data for the medical device, a detected activity level of patient 14, a detected posture of patient 14, a detected temperature of the medical device or patient, or a detected sleep state of the patient, e.g., whether the patient is asleep or awake. In some examples, computing device 24 receives the parametric patient data on a periodic, e.g., daily, basis. In some examples, the medical device that collects the parametric patient data is an IMD, such as IMD 16. In other examples, the medical device that collects the parametric patient data is another type of patient device. Examples of medical devices which may collect the parametric patient data include IMD 16, sensors 80A-80B (collectively, "sensors 80"), a wearable device, or external device 27, such as a patient programmer, a clinician programmer, or a mobile device (e.g., a smartphone) of patient 14. Wearable devices include wearable sensor 80A, wearable medical devices, or other wearable electronic devices.

In some examples, sensors 80 may be used collect parametric patient data of patient 14. Each of sensors 80 may include one or more accelerometers, pressure sensors, optical sensors for O2 saturation, etc. In some examples, sensors 80 may sense parametric patient data including one or more of an activity level of the patient, a heart rate of the patient, a posture of the patient, a cardiac electrogram of the patient, a blood pressure of the patient, accelerometer data for the patient, or other types of parametric patient data. In the example of FIG. 1, sensor 80A is a wearable sensor and sensor 80B is a non-wearable sensor. As depicted in FIG. 1, sensor 80A is positioned on an upper arm of patient 14. However, other types of wearable sensors 80 may be positioned on other body parts of patient 14, or incorporated into the apparel of patient 14, such as within clothing, shoes, eyeglasses, a watch or wristband, a hat, etc.

Computing device 24 further receives provider data for patient 14 from provider database 66 and claims database 68. For convenience, the term "provider data" is used throughout to refer to different types of medical information about patient 14, and includes the data stored by provider database 66, claims database 68, or other sources of health information not expressly depicted in FIG. 1. In some examples, the provider data may include many different types of historical medical information about patient 14. The historical medical information may include, e.g., electronic medical record (EMR) data, electronic health record (EHR) data, data from different health care providers, laboratories, clinicians, insurance companies, etc. The historical medical information may be stored across a number of different databases managed by different, unrelated entities. As one, non-limiting example, provider database 66 may store a medication history of the patient, a surgical procedure history of the patient, a hospitalization history of the patient, potassium levels of the patient over time, one or more lab test results for patient 14, a cardiovascular history of patient 14, or co-morbidities of patient 14 such as atrial fibrillation, heart failure, or diabetes, as examples. As further examples, provider database 66 may store medical images for patient 14, such as x-ray images, ultrasound images, echocardiograms, anatomical imagery, medical photographs, radiographic images, etc. Claims database 68 may store claims or payor information for patient 14, such as health records stored by an insurance provider or other payor for patient 14. Typically, the provider data is patient-specific, e.g., refers specifically to a medical history of patient 14. However, in some examples, the provider data may include broader demographic information or population-type information for a plurality of patients. For example, the provider data may include medical records for a plurality of patients of one or more population types similar to patient 14 that has had patient-specific information removed.

Computing device 24 applies a machine learning model, trained using parametric patient data and provider data for a plurality of patients, to the parametric patient data and the provider data for patient 14 to perform long-term monitoring of patient 14. In some examples, computing device 24 performs the long-term monitoring by generating a long-term probability that a cardiac arrhythmia will occur in patient 14 within a first time period (e.g., typically about 24 hours to about 48 hours). Computing device 24 determines whether the long-term probability exceeds a long-term predetermined threshold, and, in response to determining that the long-term probability exceeds the long-term predetermined threshold, transmits instructions causing IMD 16 to perform short-term monitoring of patient 14. In some examples, computing device 24 transmits the instructions to external device 27, which, in turn, transmits the instructions to IMD 16. In some examples, the long-term predetermined threshold is selected by a clinician to be a value that ensures high sensitivity in predicting cardiac arrythmia. In some examples, the long-term predetermined threshold is 50%. In some examples, the long-term predetermined threshold is another threshold, such as 75%, 80%, 90%, or 95%. In some examples, the instructions cause IMD 16 to perform the short-term monitoring by determining a short-term probability that the cardiac arrhythmia will occur in patient 14 within a second time period (e.g., typically about 30 minutes to about 60 minutes). In some examples, in response to determining that the long-term probability exceeds the long-term predetermined threshold, computing device 24 may perform other actions, such as notifying a clinician that the long-term probability has exceeded the long-term predetermined threshold or that computing system 24 has determined that patient 14 is likely to suffer a cardiac arrhythmia within the first time period.

In response to receiving the instructions from computing device 24, IMD 16 processes subsequent parametric patient data to generate the short-term probability that the cardiac arrhythmia will occur in patient 14 within the second time period. In some examples, IMD 16 generates the short-term probability by performing feature detection on the subsequent parametric patient data. In some examples, IMD 16 may analyze similar parametric patient data to the parametric patient data analyzed by computing device 24 as described above. In other examples, IMD 16 analyzes parametric patient data that is different from the parametric patient data analyzed by computing device 24. For example, computing device 24 may analyze parametric patient data that represents one or more values that are averaged over a long-term period of time (e.g., about 24 hours to about 48 hours), while IMD 16 may analyze parametric patient data that represents one or more values that are averaged over a short-term period of time (e.g., about 30 minutes to about 60 minutes).

In response to determining that the short-term probability exceeds a short-term predetermined threshold, IMD 16 performs a remediative action to reduce the short-term probability that the cardiac arrhythmia will occur in patient 14 within the second time period. In some examples, the short-term predetermined threshold is selected by a clinician to be a value that ensures high specificity in predicting cardiac arrythmia. In some examples, the short-term predetermined threshold is 95%. In some examples, the short-term predetermined threshold is another threshold, such as 80%, 90%, 99%, or 99.5%, or 99.9%.

For example, IMD 16 may issue a notification of the short-term probability that the cardiac arrhythmia will occur in patient 14 within the second time period to computing device 24 such that patient 14 or a clinician may become aware of the likelihood the cardiac arrhythmia will occur in patient 14 within the second time period. In another example, IMD 16 initiates therapy to patient 14, such as drug delivery therapy or electrical pacing therapy, to reduce the likelihood the cardiac arrhythmia will occur in patient 14 within the second time period.

In some examples, in response to the instructions from computing device 24, IMD 16 processes the parametric patient data to generate the short-term probability that the cardiac arrhythmia will occur in patient 14 and determines whether the short-term probability exceeds the short-term predetermined threshold a single time. In other examples, IMD 16 processes the parametric patient data to generate the short-term probability that the cardiac arrhythmia will occur in patient 14 and determines whether the short-term probability exceeds the short-term predetermined threshold on a continuous basis for the first time period. In other examples, IMD 16 processes the parametric patient data to generate the short-term probability that the cardiac arrhythmia will occur in patient 14 and determines whether the short-term probability exceeds the short-term predetermined threshold on a periodic basis several times during the first time period (e.g., once per 10 minutes, once per hour, once per day, etc.).

In some examples, upon determining that the likelihood the cardiac arrhythmia will occur in the patient within the first time period has been reduced, IMD 16 stops performing the short-term monitoring. For example, IMD 16 may stop processing the subsequent parametric patient data to generate the short-term probability that the cardiac arrhythmia will occur in patient 14 within the first time period. In some examples, IMD 16 stops performing the short-term monitoring after a certain amount of time has elapsed, e.g., the long-term period of time. In some examples, IMD 16 stops performing the short-term monitoring after a period of time that is longer than the long-term period of time. In some examples, IMD 16 stops performing the short-term monitoring after about 1 day. In some examples, IMD 16 stops performing the short-term monitoring after about 1 week. In some examples, the period that IMD 16 performs short-term monitoring of patient 14 is about the same as the long-term time period. In other examples, the period that IMD 16 performs short-term monitoring of patient 14 is greater than or less than the long-term time period.

In some examples, IMD 16 stops performing the short-term monitoring in response to receiving instructions from computing device 24. For example, in response to determining that the long-term probability that a cardiac arrhythmia will occur in patient 14 within the first time period has been reduced to less than the long-term predetermined threshold, computing device 24 transmits instructions to IMD 16 to stop performing the short-term monitoring.

By processing the parametric patient data to generate the short-term probability only when instructed to do so by computing device 24, IMD 16 only performs power-intensive operations, such as processing parametric patient data, when such operations are beneficial to patient 14 to prevent an imminent cardiac arrythmia. Accordingly, IMD 16 may conserve power and therefore exhibit increased battery life over conventional systems.

As depicted in the example of FIG. 1, IMD 16 is an implantable medical device that performs short-term monitoring of patient 14. However, in other examples of the techniques of the disclosure, another medical device, such as external device 27, one or more of sensors 80, a wearable medical device, or other types of devices external to patient 14 may perform the short-term monitoring of patient 14 as described herein.

In the foregoing examples, computing device 24 is a single device or distributed system that receives the parametric patient data, the provider data, and applies the machine learning model to the parametric patient data and the provider data to generate the long-term probability that a cardiac arrhythmia will occur in patient 14 within a first time period, and transmits instructions to IMD 16. However, in other examples, the functionality of computing device 24 may be performed by a group of devices. For example, an external programmer may receive the parametric patient data from IMD 16, and upload the parametric patient data to a local access point in network 25. Further, the local access point may receive, from provider database 66, the provider data for patient 14. A distributed computing system may receive, from the local access point, the parametric data and the provider data for patient 14 and apply the machine learning model to generate the long-term probability that a cardiac arrythmia will occur in patient 14 within a first time period. The distributed computing system may transmit the long-term probability to the external programmer via the local access point. The external programmer may determine that the long-term probability exceeds the long-term predetermined threshold, and in response, transmit instructions to IMD 16 causing IMD 16 to perform short-term monitoring of patient 14.

The foregoing examples describe a two-tier prediction system, e.g., computing device 24 makes a first, generalized, long-term prediction of cardiac arrythmia in patient 14, and IMD 16 makes a second, fine-grained, short-term prediction of cardiac arrythmia in patient 14. However, the techniques of the disclosure may provide for systems of varying numbers of tiers. For example, in a three-tier prediction system, computing device 24 makes a first, generalized, long-term prediction of cardiac arrythmia in patient 14, external device 7 makes a second, intermediate prediction, and IMD 16 makes a third, fine-grained, short-term prediction of cardiac arrythmia in patient 14. Other examples of the techniques of the disclosure may incorporate additional predictions at various levels to further heighten the accuracy of predicted cardiac arrythmia in patient 14 resulting in a four-, five-, or greater-tiered system.

Additionally, in the foregoing example of a two-tier prediction system, computing device 24 makes a first, generalized, long-term prediction of cardiac arrythmia in patient 14, and IMD 16 makes a second, fine-grained, short-term prediction of cardiac arrythmia in patient 14. Furthermore, in the foregoing example of a three-tier prediction system, computing device 24 makes a first, generalized, long-term prediction of cardiac arrythmia in patient 14, external device 27 makes a second, intermediate prediction, and IMD 16 makes a third, fine-grained, short-term prediction of cardiac arrythmia in patient 14. However, these predictions made by each of computing device 24, external device 27, and/or IMD 16 are provided as examples only. In other examples, each of computing device 24, external device 27, and/or IMD 16 may make predictions that are for similar or different lengths of time. For example each of computing device 24, external device 27, and/or IMD 16 may be capable of performing a long-term, intermediate or mid-term, or short-term prediction of cardiac arrythmia using the techniques described herein. For example, computing device 24 may use parametric patient data and provider data to make a short-term prediction of cardiac arrythmia in patient 14 and, in response to determining that a cardiac arrythmia is likely, transmit instructions to IMD 16 to perform generate an additional short-term prediction of cardiac arrythmia in patient 14.

Additionally, in the foregoing example of a two-tier prediction system, computing device 24 makes a first, generalized, long-term prediction of cardiac arrythmia in patient 14, and IMD 16 makes a second, fine-grained, short-term prediction of cardiac arrythmia in patient 14. In response to determining that cardiac arrythmia is likely to occur in patient 14, IMD 16 may perform a remediative action to reduce the short-term probability that the cardiac arrhythmia will occur in patient 14. However, in other examples of the techniques of the disclosure, a multi-tier system as described herein may include a different combination of devices. For example, a two-tier prediction system may include computing device 24, which makes a first, generalized, long-term prediction of cardiac arrythmia in patient 14, and external device 27, which a second, fine-grained, short-term prediction of cardiac arrythmia in patient 14 and performs a remediative action to reduce the short-term probability that the cardiac arrhythmia will occur in patient 14. As another example, a two-tier prediction system may include external device 27, which makes a first, generalized, long-term prediction of cardiac arrythmia in patient 14, and a wearable medical device, such as one of sensors 80, which performs a second, fine-grained, short-term prediction of cardiac arrythmia in patient 14 and performs a remediative action to reduce the short-term probability that the cardiac arrhythmia will occur in patient 14. In still further example, a two-tier prediction system may include external device 27, which makes a first, generalized, long-term prediction of cardiac arrythmia in patient 14, and IMD 16, which performs a second, fine-grained, short-term prediction of cardiac arrythmia in patient 14 and performs a remediative action to reduce the short-term probability that the cardiac arrhythmia will occur in patient 14.

Thus, the techniques disclosed herein may allow for enhanced patient care and increase the ability to prevent cardiac arrhythmias in a patient. For example, the knowledge that tachyarrhythmia has a relatively high likelihood of occurring within the next few days may be used to help guide preventative care for the patient. Further, the knowledge that tachyarrhythmia has a relatively high likelihood of occurring within the next few minutes or hours may be used to guide preventative therapies or emergency care for the patient. Furthermore, such a system as disclosed herein may move long-term cardiac arrhythmia prediction operations that are computationally-expensive and power consuming from a personal medical device of a patient to a cloud computing system, and activate short-term cardiac prediction operations on the medical device only when the cloud computing system predicts that a cardiac arrhythmia has a relatively high likelihood of occurring within the next few days. Thus, the techniques of the disclosure may conserve power and extend battery life of a medical device by using the medical device for cardiac prediction only when a cardiac arrhythmia has a relatively high likelihood of occurring within a particular time span.

Figure 2:
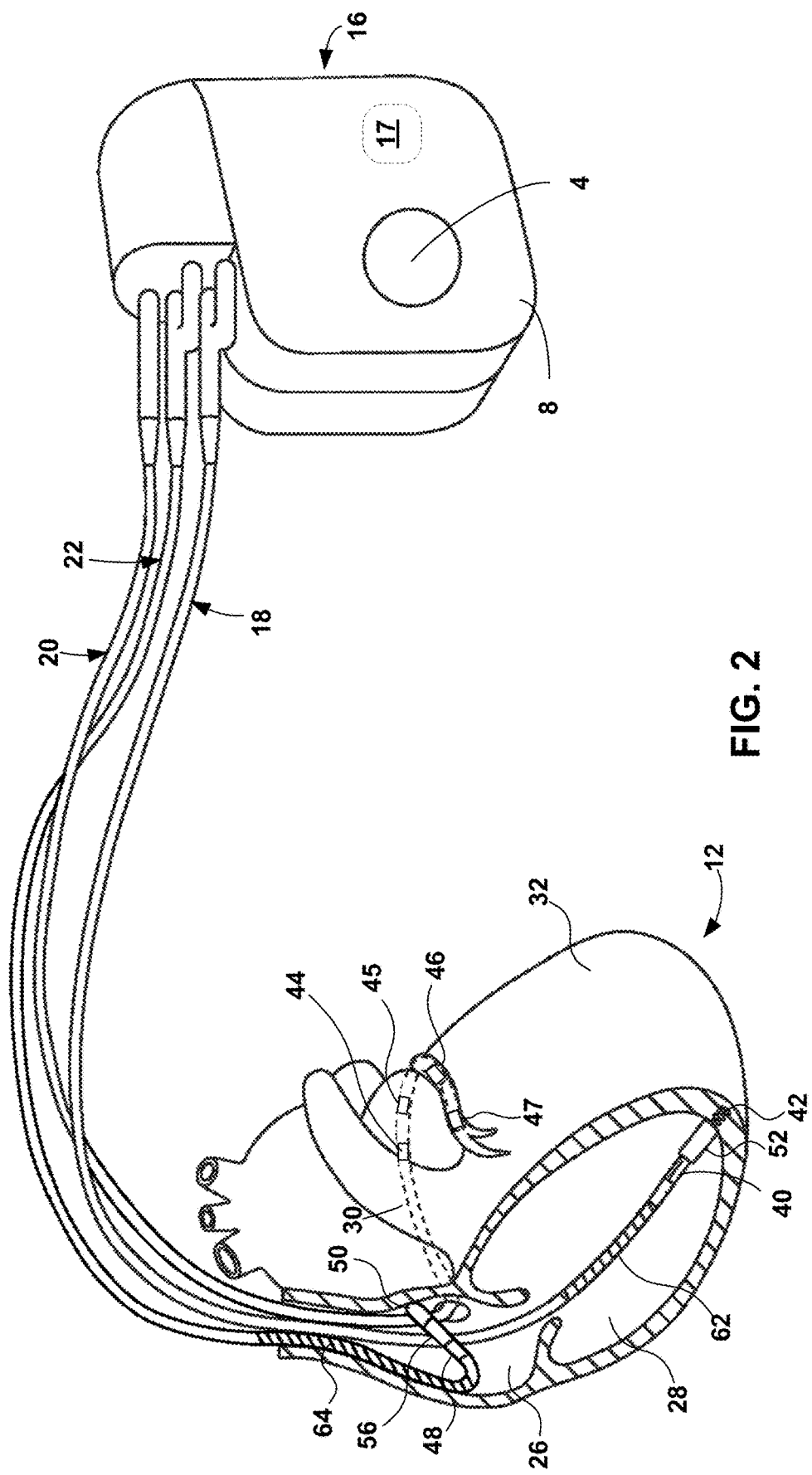
FIG. 2 is a conceptual diagram illustrating the IMD and leads of the system of FIG. 1 in greater detail.

FIG. 2 is a conceptual diagram illustrating IMD 16 and leads 18, 20, 22 of system 10 of FIG. 1 in greater detail. In the illustrated example, bipolar electrodes 40 and 42 are located adjacent to a distal end of lead 18, and bipolar electrodes 48 and 50 are located adjacent to a distal end of lead 22. In addition, four electrodes 44, 45, 46 and 47 are located adjacent to a distal end of lead 20. Lead 20 may be referred to as a quadrapolar LV lead. In other examples, lead 20 may include more or fewer electrodes. In some examples, LV lead 20 comprises segmented electrodes, e.g., in which each of a plurality of longitudinal electrode positions of the lead, such as the positions of electrodes 44, 45, 46 and 47, includes a plurality of discrete electrodes arranged at respective circumferential positions around the circumference of lead.

In the illustrated example, electrodes 40 and 44-48 take the form of ring electrodes, and electrodes 42 and 50 may take the form of extendable helix tip electrodes mounted retractably within insulative electrode heads 52 and 56, respectively. Leads 18 and 22 also include elongated electrodes 62 and 64, respectively, which may take the form of a coil. In some examples, each of electrodes 40, 42, 44-48, 50, 62, and 64 is electrically coupled to a respective conductor within the lead body of its associated lead 18, 20, 22 and thereby coupled to circuitry within IMD 16.

In some examples, IMD 16 includes one or more housing electrodes, such as housing electrode 4 illustrated in FIG. 2, which may be formed integrally with an outer surface of hermetically-sealed housing 8 of IMD 16 or otherwise coupled to housing 8. In some examples, housing electrode 4 is defined by an uninsulated portion of an outward facing portion of housing 8 of IMD 16. Other divisions between insulated and uninsulated portions of housing 8 may be employed to define two or more housing electrodes. In some examples, a housing electrode comprises substantially all of housing 8.

Housing 8 encloses signal generation circuitry that generates therapeutic stimulation, such as cardiac pacing, cardioversion, and defibrillation pulses, as well as sensing circuitry for sensing electrical signals attendant to the depolarization and repolarization of heart 12. Housing 8 may also enclose a memory for storing the sensed electrical signals. Housing 8 may also enclose a communication circuitry 17 for communication between IMD 16 and computing device 24.

IMD 16 senses electrical signals attendant to the depolarization and repolarization of heart 12 via electrodes 4, 40, 42, 44-48, 50, 62, and 64. IMD 16 may sense such electrical signals via any bipolar combination of electrodes 40, 42, 44-48, 50, 62, and 64. Furthermore, any of the electrodes 40, 42, 44-48, 50, 62, and 64 may be used for unipolar sensing in combination with housing electrode 4.

The illustrated numbers and configurations of leads 18, 20 and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intercardiac leads 18, 20 and 22, system 10 may include one or more epicardial or extravascular (e.g., subcutaneous or substernal) leads not positioned within heart 12.

In accordance with the techniques of the disclosure, IMD 16 receives instructions from computing device 24 of FIG. 1 to perform short-term monitoring of patient 14. For example, in response to receiving the instructions from computing device 24, IMD 16 processes subsequent parametric patient data to generate a short-term probability that the cardiac arrhythmia will occur in patient 14 within the second time period. In some examples, IMD 16 generates the short-term probability by performing feature detection on the subsequent parametric patient data. In some examples, IMD 16 may analyze similar parametric patient data to the parametric patient data analyzed by computing device 24 as described above. In other examples, IMD 16 analyzes parametric patient data that is different from the parametric patient data analyzed by computing device 24. For example, computing device 24 may analyze parametric patient data that represents one or more values that are averaged over a relatively long-term period of time (e.g., about 24 hours to about 48 hours), while IMD 16 may analyze parametric patient data that represents one or more values that are averaged over a relatively short-term period of time (e.g., about 30 minutes to about 60 minutes). As used throughout the disclosure, a "long-term period of time" and a "short-term period of time" are used herein to differentiate two time periods of different lengths from one another, where one of the two time periods (e.g., the "long-term period of time") has a greater length than the other of the two time periods (e.g., the "short-term period of time").

In response to determining that the short-term probability exceeds a short-term predetermined threshold, IMD 16 performs a remediative action to reduce the short-term probability that the cardiac arrhythmia will occur in patient 14 within the second time period. For example, IMD 16 may issue a notification of the short-term probability that the cardiac arrhythmia will occur in patient 14 within the second time period to computing device 24 such that patient 14 or a clinician may become aware of the likelihood the cardiac arrhythmia will occur in patient 14 within the second time period. In another example, IMD 16 initiates therapy to patient 14, such as drug delivery therapy or electrical pacing therapy, to reduce the likelihood the cardiac arrhythmia will occur in patient 14 within the second time period.

Although described herein in the context of example IMD 16 that provides therapeutic electrical stimulation, the techniques for short-term prediction of cardiac arrhythmia disclosed herein may be used with other types of devices. For example, the techniques may be implemented with an extra-cardiac defibrillator coupled to electrodes outside of the cardiovascular system, a transcatheter pacemaker configured for implantation within the heart, such as the Micra™ transcatheter pacing system commercially available from Medtronic PLC of Dublin Ireland, an insertable cardiac monitor, such as the Reveal LINQ™ ICM, also commercially available from Medtronic PLC, a neurostimulator, a drug delivery device, a wearable device such as a wearable cardioverter defibrillator, a fitness tracker, or other wearable device, a mobile device, such as a mobile phone, a "smart" phone, a laptop, a tablet computer, a personal digital assistant (PDA), or "smart" apparel such as "smart" glasses or a "smart" watch.

Thus, the techniques disclosed herein may allow for enhanced patient care and increase the ability to prevent cardiac arrhythmias in a patient. For example, the knowledge that tachyarrhythmia has a relatively high likelihood of occurring within the next few days may be used to help guide preventative care for the patient. Further, the knowledge that tachyarrhythmia has a relatively high likelihood of occurring within the next few minutes or hours may be used to guide preventative therapies or emergency care for the patient. Furthermore, such a system as disclosed herein may activate short-term cardiac prediction operations on a medical device only in response to the cloud computing system predicting that a cardiac arrhythmia has a relatively high likelihood of occurring within the next few days. Thus, the techniques of the disclosure may conserve power and extend battery life of a medical device by using the medical device for cardiac prediction only when a cardiac arrhythmia has a relatively high likelihood of occurring within a particular time span.

Figure 3:
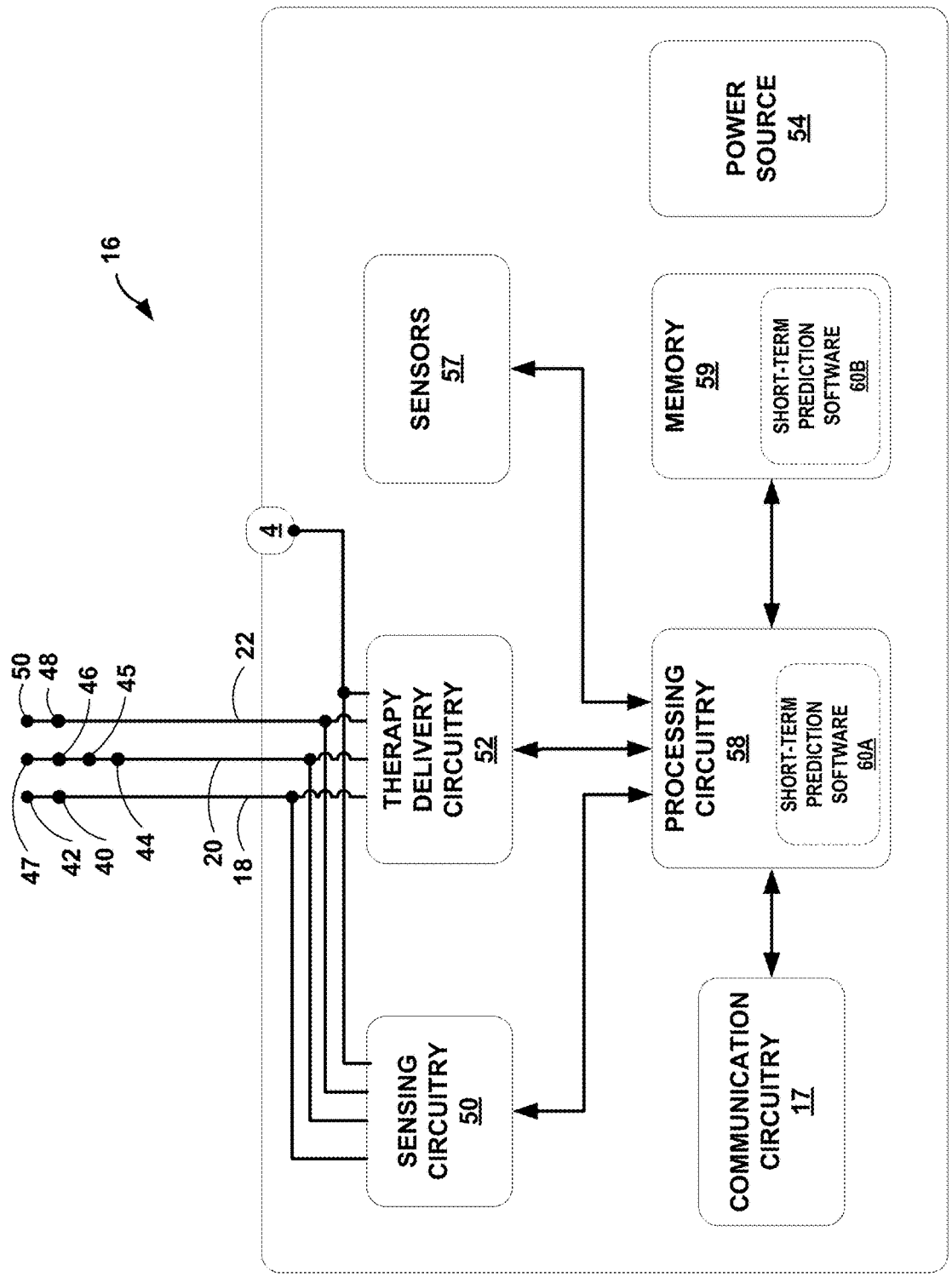
FIG. 3 is a block diagram of an example implantable medical device according to the techniques of the disclosure.

FIG. 3 is a block diagram of example IMD 16 according to the techniques of the disclosure. In the illustrated example, IMD 16 includes processing circuitry 58, memory 59, communication circuitry 17, sensing circuitry 50, therapy delivery circuitry 52, sensors 57, and power source 54. Memory 59 includes computer-readable instructions that, when executed by processing circuitry 58, cause IMD 16 and processing circuitry 58 to perform various functions attributed to IMD 16 and processing circuitry 58 herein (e.g., performing short-term prediction of cardiac arrhythmias, delivering therapy, such as anti-tachycardia pacing, bradycardia pacing, and post-shock pacing therapy, etc.). Memory 59 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 58 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 58 may include multiple components, such as any combination of one or more microprocessors, one or more controllers, one or more DSPs, one or more ASICs, or one or more FPGAs, as well as other discrete or integrated logic circuitry. The functions attributed to processing circuitry 58 herein may be embodied as software, firmware, hardware or any combination thereof.

Processing circuitry 58 controls therapy delivery circuitry 52 to deliver stimulation therapy to heart 5 according to therapy parameters, which may be stored in memory 59. For example, processing circuitry 58 may control therapy delivery circuitry 52 to deliver electrical pulses with the amplitudes, pulse widths, frequency, or electrode polarities specified by the therapy parameters. In this manner, therapy delivery circuitry 52 may deliver pacing pulses (e.g., ATP pulses, bradycardia pacing pulses, or post-shock pacing therapy) to heart 5 via electrodes 34 and 40. In some examples, therapy delivery circuitry 52 may deliver pacing stimulation, e.g., ATP therapy, bradycardia therapy, or post-shock pacing therapy, in the form of voltage or current electrical pulses. In other examples, therapy delivery circuitry 52 may deliver one or more of these types of stimulation in the form of other signals, such as sine waves, square waves, or other substantially continuous time signals.

Therapy delivery circuitry 52 is electrically coupled to electrodes 34 and 40 carried on the housing of IMD 16. Although IMD 16 may only include two electrodes, e.g., electrodes 34 and 40, in other examples, IMD 16 may utilize three or more electrodes. IMD 16 may use any combination of electrodes to deliver therapy and/or detect electrical signals from patient 12. In some examples, therapy delivery circuitry 52 includes a charging circuit, one or more pulse generators, capacitors, transformers, switching modules, and/or other components capable of generating and/or storing energy to deliver as pacing therapy, cardiac resynchronization therapy, other therapy or a combination of therapies. In some examples, therapy delivery circuitry 52 delivers therapy as one or more electrical pulses according to one or more therapy parameter sets defining an amplitude, a frequency, a voltage or current of the therapy, or other parameters of the therapy.

Sensing circuitry 50 monitors signals from one or more combinations (also referred to as vectors) of two or more electrodes from among electrodes 4, 40, 42, 44-48, 50, 62, and 64 in order to monitor electrical activity of heart 12, impedance, or other electrical phenomenon. In some examples, sensing circuitry 50 includes one or more analog components, digital components or a combination thereof. In some examples, sensing circuitry 50 includes one or more sense amplifiers, comparators, filters, rectifiers, threshold detectors, analog-to-digital converters (ADCs) or the like. In some examples, sensing circuitry 50 converts sensed signals to digital form and provides the digital signals to processing circuitry 58 for processing or analysis. In one example, sensing circuitry 50 amplifies signals from electrodes 4, 40, 42, 44-48, 50, 62, and 64 and converts the amplified signals to multi-bit digital signals by an ADC.

In some examples, sensing circuitry 50 performs sensing of the cardiac electrogram to determine heart rates or heart rate variability, or to detect arrhythmias (e.g., tachyarrhythmias or bradycardia) or to sense other parameters or events from the cardiac electrogram. Sensing circuitry 50 may also include a switching circuitry to select which of the available electrodes (and the electrode polarity) are used to sense the heart activity, depending upon which electrode combination, or electrode vector, is used in the current sensing configuration. Processing circuitry 58 may control the switching circuitry to select the electrodes that function as sense electrodes and their polarity. Sensing circuitry 50 may include one or more detection channels, each of which may be coupled to a selected electrode configuration for detection of cardiac signals via that electrode configuration. In some examples, sensing circuitry 50 compares processed signals to a threshold to detect the existence of atrial or ventricular depolarizations and indicate the existence of the atrial depolarization (e.g., P-waves) or ventricular depolarizations (e.g., R-waves) to processing circuitry 58. Sensing circuitry 50 may comprise one or more amplifiers or other circuitry for comparison of the cardiac electrogram amplitude to a threshold, which may be adjustable.

Processing circuitry 58 may include a timing and control module, which may be embodied as hardware, firmware, software, or any combination thereof. The timing and control module may comprise a dedicated hardware circuit, such as an ASIC, separate from other processing circuitry 58 components, such as a microprocessor, or a software module executed by a component of processing circuitry 58, which may be a microprocessor or ASIC. The timing and control module may implement programmable counters. If IMD 16 is configured to generate and deliver bradycardia pacing pulses to heart 12, such counters may control the basic time intervals associated with DDD, VVI, DVI, VDD, AAI, DDI, DDDR, VVIR, DVIR, VDDR, AAIR, DDIR and other modes of pacing.

Memory 59 may be configured to store a variety of operational parameters, therapy parameters, sensed and detected data, and any other information related to the therapy and treatment of patient 12. In the example of FIG. 3, memory 58 may store sensed cardiac EGMs, e.g., associated with detected or predicted arrhythmias, and therapy parameters that define the delivery of therapy provided by therapy delivery circuitry 52. In other examples, memory 58 may act as a temporary buffer for storing data until it can be uploaded to computing device 24.

Communication circuitry 17 includes any suitable circuitry, firmware, software, or any combination thereof for communicating with another device, such as computing device 24 via network 25 of FIG. 1. For example, communication circuitry 17 may include one or more antennae, modulation and demodulation circuitry, filters, amplifiers, or the like for radio frequency communication with other devices, such as computing device 24 via network 25. Under the control of processing circuitry 58, communication circuitry 17 may receive downlink telemetry from and send uplink telemetry to computing device 24 with the aid of an antenna, which may be internal and/or external. Processing circuitry 58 may provide the data to be uplinked to computing device 24 and the control signals for the telemetry circuit within communication circuitry 17, e.g., via an address/data bus. In some examples, communication circuitry 17 may provide received data to processing circuitry 58 via a multiplexer.

Power source 54 may be any type of device that is configured to hold a charge to operate the circuitry of IMD 16. Power source 54 may be provided as a rechargeable or non-rechargeable battery. In other example, power source 54 may incorporate an energy scavenging system that stores electrical energy from movement of IMD 16 within patient 12.

In accordance with the techniques of the disclosure, IMD 16 collects, via sensing circuitry 50 and/or sensors 57, parametric patient data of patient 14. Sensors 57 may include one or more sensors, such as one or more accelerometers, pressure sensors, optical sensors for O2 saturation, etc. In some examples, the parametric patient data includes one or more of an activity level of the patient, a heart rate of the patient, a posture of the patient, a cardiac electrogram of the patient, a blood pressure of the patient, accelerometer data for the patient, or other types of parametric patient data. IMD 16 uploads, via communication circuitry 17, the parametric patient data to computing device 24 over network 25 and/or to one or more of sensors 80 or external device 27. The activity level may, in some examples, be a summation of activity over a period of time, such as one or more seconds or minutes. In some examples, IMD 16 uploads the parametric patient data to computing device 24, external device 27 and/or sensors 80 on a daily basis. In some examples, the parametric patient data includes one or more values that represent average measurements of patient 14 over a long-term time period (e.g., about 24 hours to about 48 hours). In this example, IMD 16 both uploads the parametric patient data to computing device 24 and performs short-term monitoring of patient 14 (as described below). However, in other examples, the medical device that collects the parametric patient data is different from the medical device that performs short-term monitoring of patient 14. For example, one or more other devices, such as a wearable medical device or a mobile device (e.g., a smartphone) of patient 14, may collect the parametric patient data and upload the parametric patient data to computing device 24.

In some examples, processing circuitry 58 receives instructions from computing device 24 of FIG. 1 to perform short-term monitoring of patient 14. For example, in response to receiving the instructions from computing device 24, processing circuitry 58 executes short-term prediction software 60A stored in memory 59 as short-term prediction software 60B. For example, processing circuitry 58 may execute short-term prediction software 60A to process subsequent parametric patient data to generate a short-term probability that the cardiac arrhythmia will occur in patient 14 within a short-term time period. In some examples, processing circuitry 58 generates the short-term probability by performing feature detection on subsequent parametric patient data sensed by sensing circuitry 50. In some examples, processing circuitry 58 performs feature detection on one or more of electrocardiogram data, electrode impedance measurements, accelerometer data, temperature data for patient 14, or audio data of a heart of patient 14.

As an example, processing circuitry 58 performs feature detection on subsequent parametric patient data, including electrocardiogram data. In this example, the parametric patient data includes one or more of an average frequency or an average amplitude of a T-wave of an electrocardiogram of patient 14. Processing circuitry 58 receives a raw electrocardiogram signal from via sensing circuitry 50 and/or sensors 57, and extracts features from the raw electrocardiogram signal. In some examples, processing circuitry 58 identifies one or more of T-wave alternans, QRS morphology measures, etc. For example, processing circuitry 58 identifies one or more features of a T-wave of an electrocardiogram of patient 14 and applies a model to the one or more identified features to generate the short-term probability that the cardiac arrhythmia will occur in patient 14 within the short-term time period. In some examples, the one or more identified features are one or more amplitudes of the T-wave. In some examples, the one or more identified features are a frequency of the T-wave. In some examples, the one or more identified features include at least an amplitude of the T-wave and a frequency of the T-wave.

In some examples, processing circuitry 58 identifies one or more relative changes in one or more identified features of the parametric patient data that are predicative of subsequent cardiac arrythmia in patient 14. In some examples, processing circuitry 58 identifies one or more interactions between multiple identified features that are predicative of subsequent cardiac arrythmia in patient 14. In some examples, processing circuitry 58 analyzes parametric patient data that represents one or more values that are averaged over a short-term period of time (e.g., about 30 minutes to about 60 minutes).

In some examples, processing circuitry 58 may use the identified features as an input to a second machine learning model that generates, as an output of the second machine learning model, the short-term probability that the cardiac arrhythmia will occur in patient 14 within a short-term time period. In another example, processing circuitry 58 uses the raw signal obtained via sensing circuitry 50 and/or sensors 57 as a direct input to the second machine learning model that generates the short-term probability. In some examples, the second machine learning model is trained using parametric patient data and provider data for a plurality of patients in a similar fashion to the training process described above for the machine learning model of computing device 24. In some examples, the second machine learning model performs error-correction based on received feedback indicating whether a cardiac arrythmia occurred in patient 14 so as to incrementally improve predictions made by the second machine learning model by "learning" from correct and incorrect predictions made by the second machine learning model in the past. Further, the training process may be used to further fine-tune the second machine learning model that is trained using population-based data to provide more accurate predictions for a particular individual.

Processing circuitry 58 compares the short-term probability that the cardiac arrhythmia will occur in patient 14 within a short-term time period to a predetermined threshold. In response to determining that the short-term probability exceeds the predetermined threshold, processing circuitry 58 performs a remediative action to reduce the short-term probability that the cardiac arrhythmia will occur in patient 14 within the short-term time period. For example, processing circuitry 58 may issue, via communication circuitry 17, a notification of the short-term probability that the cardiac arrhythmia will occur in patient 14 within the short-term time period to computing device 24 such that patient 14 or a clinician may become aware of the likelihood the cardiac arrhythmia will occur in patient 14 within the short-term time period. In another example, processing circuitry 58 causes therapy delivery circuitry 52 to initiate delivery of therapy to patient 14. While in the example of FIG. 3, therapy delivery circuitry 52 is configured to deliver electrical stimulation therapy or electrical pacing therapy, in other examples, processing circuitry 58 may cause, e.g., a drug delivery system to deliver drug therapy to patient 14. Accordingly, processing circuitry 58 may perform a remediative action to reduce the likelihood the cardiac arrhythmia will occur in patient 14 within the short-term time period.

Although described herein in the context of example IMD 16 that provides therapeutic electrical stimulation, the techniques for short-term prediction of cardiac arrhythmia disclosed herein may be used with other types of devices. For example, the techniques may be implemented with a transcatheter pacemaker configured for implantation within the heart, such as the Micra™ transcatheter pacing system commercially available from Medtronic PLC of Dublin Ireland, an insertable cardiac monitor, such as the Reveal LINQ™ ICM, also commercially available from Medtronic PLC, a neurostimulator, a drug delivery device, a wearable device such as a wearable cardioverter defibrillator, a fitness tracker, or other wearable device, a mobile device, such as a mobile phone, a "smart" phone, a laptop, a tablet computer, a personal digital assistant (PDA), or "smart" apparel such as "smart" glasses or a "smart" watch.

Thus, the techniques disclosed herein may allow for enhanced patient care and increase the ability to prevent cardiac arrhythmias in a patient. For example, the knowledge that tachyarrhythmia has a relatively high likelihood of occurring within the next few minutes or hours may be used to guide preventative therapies or emergency care for the patient. Furthermore, such a system as disclosed herein may activate short-term cardiac prediction operations on a medical device only in response to computing device 24 predicting that a cardiac arrhythmia has a relatively high likelihood of occurring within the next few days. Thus, the techniques of the disclosure may conserve power and extend battery life of IMD 16 by using IMD 16 for cardiac prediction only when a cardiac arrhythmia has a relatively high likelihood of occurring within a particular time span.

Figure 4:
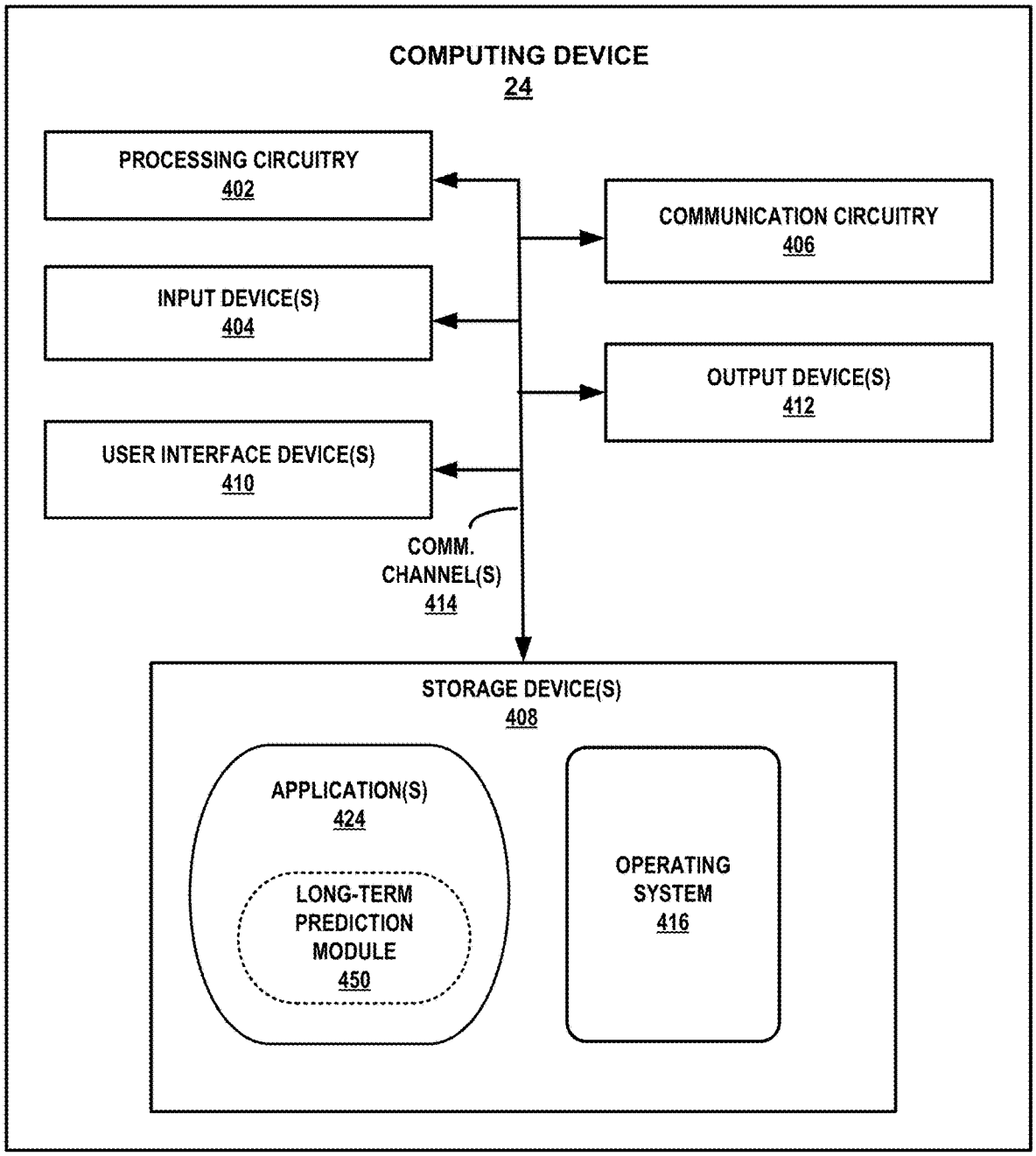
FIG. 4 is a block diagram illustrating an example computing device that operates in accordance with one or more techniques of the present disclosure.

FIG. 4 is a block diagram illustrating an example computing device 24 that operates in accordance with one or more techniques of the present disclosure. In one example, computing device 24 includes processing circuitry 402 for executing applications 424 that include long-term prediction module 450 or any other applications described herein. Although shown in FIG. 4 as a stand-alone computing device 24 for purposes of example, computing device 24 may be any component or system that includes processing circuitry or other suitable computing environment for executing software instructions and, for example, need not necessarily include one or more elements shown in FIG. 4 (e.g., communication circuitry 406; and in some examples components such as storage device(s) 408 may not be co-located or in the same chassis as other components). In some examples, computing device 24 may be a cloud computing system distributed across a plurality of devices.

As shown in the example of FIG. 4, computing device 24 includes processing circuitry 402, one or more input devices 404, communication circuitry 406, one or more output devices 412, one or more storage devices 408, and user interface (UI) device(s) 410. Computing device 24, in one example, further includes one or more application(s) 424 such as long-term prediction module 450, and operating system 416 that are executable by computing device 24. Each of components 402, 404, 406, 408, 410, and 412 are coupled (physically, communicatively, and/or operatively) for inter-component communications. In some examples, communication channels 414 may include a system bus, a network connection, an inter-process communication data structure, or any other method for communicating data. As one example, components 402, 404, 406, 408, 410, and 412 may be coupled by one or more communication channels 414.

Processing circuitry 402, in one example, is configured to implement functionality and/or process instructions for execution within computing device 24. For example, processing circuitry 402 may be capable of processing instructions stored in storage device 408. Examples of processing circuitry 402 may include, any one or more of a microprocessor, a controller, a digital signal processor (DSP), an application specific integrated circuit (ASIC), a field-programmable gate array (FPGA), or equivalent discrete or integrated logic circuitry.

One or more storage devices 408 may be configured to store information within computing device 24 during operation. Storage device 408, in some examples, is described as a computer-readable storage medium. In some examples, storage device 408 is a temporary memory, meaning that a primary purpose of storage device 408 is not long-term storage. Storage device 408, in some examples, is described as a volatile memory, meaning that storage device 408 does not maintain stored contents when the computer is turned off. Examples of volatile memories include random access memories (RAM), dynamic random access memories (DRAM), static random access memories (SRAM), and other forms of volatile memories known in the art. In some examples, storage device 408 is used to store program instructions for execution by processing circuitry 402. Storage device 408, in one example, is used by software or applications 424 running on computing device 24 to temporarily store information during program execution.

Storage devices 408, in some examples, also include one or more computer-readable storage media. Storage devices 408 may be configured to store larger amounts of information than volatile memory. Storage devices 408 may further be configured for long-term storage of information. In some examples, storage devices 408 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Computing device 24, in some examples, also includes communication circuitry 406. Computing device 24, in one example, utilizes communication circuitry 406 to communicate with external devices, such as IMD 16 and provider database 66 of FIG. 1. Communication circuitry 406 may include a network interface card, such as an Ethernet card, an optical transceiver, a radio frequency transceiver, or any other type of device that can send and receive information. Other examples of such network interfaces may include 3G, 4G, 5G, and WiFi radios.

Computing device 24, in one example, also includes one or more user interface devices 410. User interface devices 410, in some examples, are configured to receive input from a user through tactile, audio, or video feedback. Examples of user interface device(s) 410 include a presence-sensitive display, a mouse, a keyboard, a voice responsive system, video camera, microphone or any other type of device for detecting a command from a user. In some examples, a presence-sensitive display includes a touch-sensitive screen.

One or more output devices 412 may also be included in computing device 24. Output device 412, in some examples, is configured to provide output to a user using tactile, audio, or video stimuli. Output device 412, in one example, includes a presence-sensitive display, a sound card, a video graphics adapter card, or any other type of device for converting a signal into an appropriate form understandable to humans or machines. Additional examples of output device 412 include a speaker, a cathode ray tube (CRT) monitor, a liquid crystal display (LCD), or any other type of device that can generate intelligible output to a user.

Computing device 24 may include operating system 416. Operating system 416, in some examples, controls the operation of components of computing device 24. For example, operating system 416, in one example, facilitates the communication of one or more applications 424 and long-term prediction module 450 with processing circuitry 402, communication circuitry 406, storage device 408, input device 404, user interface devices 410, and output device 412.

Application 424 may also include program instructions and/or data that are executable by computing device 24. Example application(s) 424 executable by computing device 24 may include long-term prediction module 450. Other additional applications not shown may alternatively or additionally be included to provide other functionality described herein and are not depicted for the sake of simplicity.

In accordance with the techniques of the disclosure, applications 424 include long-term prediction module 450. In one example, processing circuitry 402 executes long-term prediction module 450 to provide long-term prediction of cardiac ventricular arrhythmias of patient 14 of FIG. 1. In one example, long-term prediction module 450 includes a machine learning model that generates, based on parametric patient data and provider data for patient 14, a long-term probability that a cardiac arrhythmia will occur in patient 14 within a long-term time period (e.g., typically about 24 hours to about 48 hours). In some examples, the machine learning model is generated by a neural network system, a deep learning system, or other type of supervised or unsupervised machine learning system. For example, the machine learning model may be generated by a feedforward neural network, such as a convolutional neural network, a radial basis function neural network, a recurrent neural network, a modular or associative neural network. In some examples, long-term prediction module 450 trains the machine learning model with parametric patient data and provider data for a plurality of patients to generate the long-term probability. In some examples, after the machine learning model has been pre-trained with the parametric patient data and provider data for the plurality of patients, long-term prediction module 450 further trains the machine learning model with parametric patient data and provider data specific to patient 14.

In some examples, long-term prediction module 450 trains the machine learning model with the parametric patient data and provider data for the plurality of patients, determines an error rate of the machine learning model, and then feeds the error rate back to the machine learning model so as to allow the machine learning model to update its predictions based on the error rate. In some examples, long-term prediction module 450 may receive, from patient 14 or a clinician, feedback indicating whether a predicted cardiac arrhythmia occurred in patient 14 within the first time period. In some examples, long-term prediction module 450 may receive, from IMD 16, a message indicating that IMD 16 has detected (or has not detected) an occurrence of cardiac arrhythmia in patient 14 and whether a cardiac arrhythmia in patient 14 was predicted (or was not predicted). In some examples, long-term prediction module 450 may obtain the feedback in other ways, such as by periodically checking the provider data to determine if a cardiac arrythmia occurred. Long-term prediction module 450 may update the machine learning model with the feedback indicating whether the predicted cardiac arrhythmia occurred in patient 14 within the first time period. Thus, the training process may occur iteratively so as to incrementally improve predictions made by the machine learning model by "learning" from correct and incorrect predictions made by the machine learning model in the past. Further, the training process may be used to further fine-tune a machine learning model that is trained using population-based data to provide more accurate predictions for a particular individual.

Once the machine learning model has been trained to generate long-term probabilities that a cardiac arrhythmia will occur in patient 14 within a long-term time period that are of a threshold accuracy selected by the clinician, long-term prediction module 450 may use the machine learning model to provide long-term prediction of cardiac ventricular arrhythmias of patient 14. For example, long-term prediction module 450, executed by processing circuitry 402, receives, via communication circuitry 406, parametric patient data collected by a medical device of patient 14. In some examples, the parametric patient data includes one or more of an activity level of the patient, a heart rate of the patient, a posture of the patient, a cardiac electrogram of the patient, a blood pressure of the patient, accelerometer data for the patient, or other types of parametric patient data. In some examples, the medical device that collects the parametric patient data is an IMD, such as IMD 16 of FIG. 1. In other examples, the medical device that collects the parametric patient data is another type of patient device, such as a wearable medical device or a mobile device (e.g., a smartphone) of patient 14. In some examples, long-term prediction module 450 receives the parametric patient data from IMD 16 on a daily basis.

Long-term prediction module 450 further receives, via communication circuitry 406, provider data for patient 14 from provider database 66. In some examples, the provider data stored by provider database 66 may include many different types of historical medical information about patient 14. For example, provider database 66 may store a medication history of the patient, a surgical procedure history of the patient, a hospitalization history of the patient, potassium levels of the patient over time, or one or more lab test results for the patient, etc.

Long-term prediction module 450 applies the trained machine learning model to the parametric patient data and the provider data for patient 14 to perform long-term monitoring of patient 14. In some examples, long-term prediction module 450 performs the long-term monitoring by generating a long-term probability that a cardiac arrhythmia will occur in patient 14 within a long-term time period (e.g., typically about 24 hours to about 48 hours). For example, long-term prediction module 450 applies the trained machine learning model to the parametric patient data and the provider data for patient 14 to generate the long-term probability that a cardiac arrhythmia will occur in patient 14 within the long-term time period. For example, the machine learning model may convert the parametric patient data and the provider data into one or more vectors and tensors (e.g., multi-dimensional arrays) that represent the parametric patient data and the provider data. The machine learning model may apply mathematical operations to the one or more vectors and tensors to generate a mathematical representation of the parametric patient data and the provider data. The machine learning model may determine different weights that correspond to identified relationships between the parametric patient data and the provider data and the occurrence of cardiac arrhythmia within the long-term time period. The machine learning model may apply the different weights to the parametric patient data and the provider data to generate the long-term probability that a cardiac arrhythmia will occur in patient 14 within the long-term time period.

In some examples, long-term prediction module 450 determines whether the determined long-term probability that a cardiac arrhythmia will occur in patient 14 within a long-term time period exceeds a predetermined threshold set by a clinician. In response to determining that the long-term probability exceeds the predetermined threshold, long-term prediction module 450 transmits, via communication circuitry 406, instructions to IMD 16 causing IMD 16 to perform short-term monitoring of patient 14 as described above. Additionally or alternatively, in response to determining that the long-term probability exceeds the predetermined threshold, long-term prediction module 450 transmits, via communication circuitry 406, instructions to external device 27 causing external device 27 to perform mid-term monitoring of patient 14 as described below. In some examples, in response to determining that the long-term probability exceeds the predetermined threshold, long-term prediction module 450 may perform other actions, such as notifying, via output device 412, a clinician that the long-term probability has exceeded the predetermined threshold or that long-term prediction module 450 has determined that patient 14 is likely to suffer a cardiac arrhythmia within the long-term time period.

Thus, the techniques disclosed herein may allow for enhanced patient care and increase the ability to prevent cardiac arrhythmias in a patient. For example, the knowledge that tachyarrhythmia has a relatively high likelihood of occurring within the next few days may be used to help guide preventative care for the patient. Furthermore, such a system as disclosed herein may move long-term cardiac arrhythmia prediction operations that are computationally-expensive and power consuming from a personal medical device of a patient to a cloud computing system, and activate short-term cardiac prediction operations on the medical device only when the cloud computing system predicts that a cardiac arrhythmia has a relatively high likelihood of occurring within the next few days. Thus, the techniques of the disclosure may conserve power and extend battery life of a medical device by using the medical device for cardiac prediction only when a cardiac arrhythmia has a relatively high likelihood of occurring within a particular time span.

Figure 5:
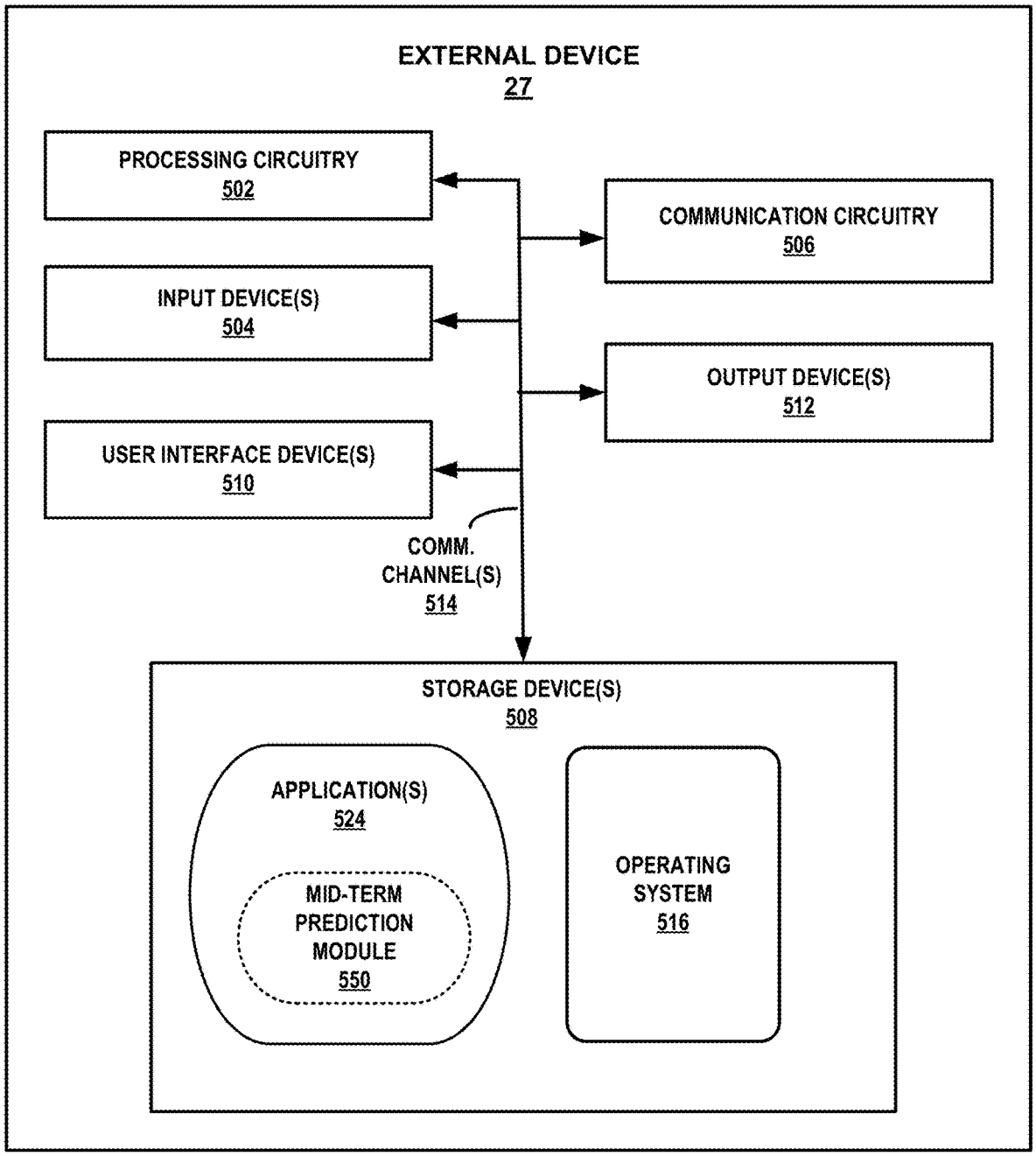
FIG. 5 is a block diagram illustrating an example external device that operates in accordance with one or more techniques of the present disclosure.

FIG. 5 is a block diagram illustrating an example external device 27 that operates in accordance with one or more techniques of the present disclosure. In some examples, external device 27 takes the form of an external programmer or mobile device, such as a mobile phone, a "smart" phone, a laptop, a tablet computer, a personal digital assistant (PDA), a wearable electronic device, etc. In some examples, external device 27 is a CareLink™ monitor available from Medtronic, Inc.

In one example, external device 27 includes processing circuitry 502 for executing applications 524 that include mid-term prediction module 550 or any other applications described herein. Although shown in FIG. 5 as a stand-alone external device 27 for purposes of example, external device 27 may be any component or system that includes processing circuitry or other suitable computing environment for executing software instructions and, for example, need not necessarily include one or more elements shown in FIG. 5 (e.g., communication circuitry 506; and in some examples components such as storage device(s) 508 may not be co-located or in the same chassis as other components).

As shown in the example of FIG. 5, external device 27 includes processing circuitry 502, one or more input devices 504, communication circuitry 506, one or more output devices 512, one or more storage devices 508, and user interface (UI) device(s) 510. External device 27, in one example, further includes one or more application(s) 524 such as mid-term prediction module 550, and operating system 516 that are executable by external device 27. Each of components 502, 504, 506, 508, 510, and 512 are coupled (physically, communicatively, and/or operatively) for inter-component communications. In some examples, communication channels 514 may include a system bus, a network connection, an inter-process communication data structure, or any other method for communicating data. As one example, components 502, 504, 506, 508, 510, and 512 may be coupled by one or more communication channels 514.

Processing circuitry 502, in one example, is configured to implement functionality and/or process instructions for execution within external device 27. For example, processing circuitry 502 may be capable of processing instructions stored in storage device 508. Examples of processing circuitry 502 may include, any one or more of a microprocessor, a controller, a digital signal processor (DSP), an application specific integrated circuit (ASIC), a field-programmable gate array (FPGA), or equivalent discrete or integrated logic circuitry.

One or more storage devices 508 may be configured to store information within external device 27 during operation. Storage device 508, in some examples, is described as a computer-readable storage medium. In some examples, storage device 508 is a temporary memory, meaning that a primary purpose of storage device 508 is not long-term storage. Storage device 508, in some examples, is described as a volatile memory, meaning that storage device 508 does not maintain stored contents when the computer is turned off. Examples of volatile memories include random access memories (RAM), dynamic random access memories (DRAM), static random access memories (SRAM), and other forms of volatile memories known in the art. In some examples, storage device 508 is used to store program instructions for execution by processing circuitry 502. Storage device 508, in one example, is used by software or applications 524 running on external device 27 to temporarily store information during program execution.

Storage devices 508, in some examples, also include one or more computer-readable storage media. Storage devices 508 may be configured to store larger amounts of information than volatile memory. Storage devices 508 may further be configured for long-term storage of information. In some examples, storage devices 508 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

External device 27, in some examples, also includes communication circuitry 506. External device 27, in one example, utilizes communication circuitry 506 to communicate with external devices, such as IMD 16 and computing device 24 of FIG. 1. Communication circuitry 506 may include a network interface card, such as an Ethernet card, an optical transceiver, a radio frequency transceiver, or any other type of device that can send and receive information. Other examples of such network interfaces may include 3G, 4G, 5G, and WiFi radios.

External device 27, in one example, also includes one or more user interface devices 510. User interface devices 510, in some examples, are configured to receive input from a user through tactile, audio, or video feedback. Examples of user interface device(s) 510 include a presence-sensitive display, a mouse, a keyboard, a voice responsive system, video camera, microphone or any other type of device for detecting a command from a user. In some examples, a presence-sensitive display includes a touch-sensitive screen.

One or more output devices 512 may also be included in external device 27. Output device 512, in some examples, is configured to provide output to a user using tactile, audio, or video stimuli. Output device 512, in one example, includes a presence-sensitive display, a sound card, a video graphics adapter card, or any other type of device for converting a signal into an appropriate form understandable to humans or machines. Additional examples of output device 512 include a speaker, a cathode ray tube (CRT) monitor, a liquid crystal display (LCD), or any other type of device that can generate intelligible output to a user.

External device 27 may include operating system 516. Operating system 516, in some examples, controls the operation of components of external device 27. For example, operating system 516, in one example, facilitates the communication of one or more applications 524 and mid-term prediction module 550 with processing circuitry 502, communication circuitry 506, storage device 508, input device 504, user interface devices 510, and output device 512.

Application 524 may also include program instructions and/or data that are executable by external device 27. Example application(s) 524 executable by external device 27 may include mid-term prediction module 550. Other additional applications not shown may alternatively or additionally be included to provide other functionality described herein and are not depicted for the sake of simplicity.

In accordance with the techniques of the disclosure, applications 524 include mid-term prediction module 550. In one example, processing circuitry 502 executes mid-term prediction module 550 to provide mid-term prediction of cardiac ventricular arrhythmias of patient 14 of FIG. 1. In one example, mid-term prediction module 550 includes a machine learning model that generates, based on parametric patient data and provider data for patient 14, a mid-term probability that a cardiac arrhythmia will occur in patient 14 within a mid-term time period (e.g., typically about 24 hours to about 48 hours). In some examples, the machine learning model is generated by a neural network system, a deep learning system, or other type of supervised or unsupervised machine learning system. For example, the machine learning model may be generated by a feedforward neural network, such as a convolutional neural network, a radial basis function neural network, a recurrent neural network, a modular or associative neural network. In some examples, mid-term prediction module 550 trains the machine learning model with parametric patient data and provider data for a plurality of patients to generate the mid-term probability. In some examples, after the machine learning model has been pre-trained with the parametric patient data and provider data for the plurality of patients, mid-term prediction module 550 further trains the machine learning model with parametric patient data and provider data specific to patient 14. While in the foregoing example, the mid-term prediction module 550 trains the machine learning model with both parametric patient data and provider data for a plurality of patients, in some examples, the mid-term prediction module 550 trains the machine learning model with only parametric patient data and not provider data or with only provider data and not parametric patient data.

In some examples, mid-term prediction module 550 trains the machine learning model with the parametric patient data and provider data for the plurality of patients, determines an error rate of the machine learning model, and then feeds the error rate back to the machine learning model so as to allow the machine learning model to update its predictions based on the error rate. In some examples, mid-term prediction module 550 may receive, from patient 14 or a clinician, feedback indicating whether a predicted cardiac arrhythmia occurred in patient 14 within the first time period. In some examples, mid-term prediction module 550 may receive, from IMD 16, a message indicating that IMD 16 has detected (or has not detected) an occurrence of cardiac arrhythmia in patient 14 and whether a cardiac arrhythmia in patient 14 was predicted (or was not predicted). In some examples, mid-term prediction module 550 may obtain the feedback in other ways, such as by periodically checking the provider data to determine if a cardiac arrythmia occurred. Mid-term prediction module 550 may update the machine learning model with the feedback indicating whether the predicted cardiac arrhythmia occurred in patient 14 within the first time period. Thus, the training process may occur iteratively so as to incrementally improve predictions made by the machine learning model by "learning" from correct and incorrect predictions made by the machine learning model in the past. Further, the training process may be used to further fine-tune a machine learning model that is trained using population-based data to provide more accurate predictions for a particular individual.

Once the machine learning model has been trained to generate mid-term probabilities that a cardiac arrhythmia will occur in patient 14 within a mid-term time period that are of a threshold accuracy selected by the clinician, mid-term prediction module 550 may use the machine learning model to provide mid-term prediction of cardiac ventricular arrhythmias of patient 14. For example, mid-term prediction module 550, executed by processing circuitry 502, receives, via communication circuitry 506, parametric patient data collected by a medical device of patient 14. In some examples, mid-term prediction module 550 may also receive other parametric patient data collected by external device 27, such as geographic location, accelerometer data, or input from patient 14. In some examples, the parametric patient data includes one or more of an activity level of the patient, a heart rate of the patient, a posture of the patient, a cardiac electrogram of the patient, a blood pressure of the patient, accelerometer data for the patient, or other types of parametric patient data. In some examples, the medical device that collects the parametric patient data is an IMD, such as 1 MB 16 of FIG. 1. In other examples, the medical device that collects the parametric patient data is another type of patient device, such as a wearable medical device, wearable sensor such as sensors 80 of FIG. 1, or a mobile device (e.g., a smartphone) of patient 14. In some examples, mid-term prediction module 550 receives the parametric patient data from IMD 16 and/or sensors 80 on a daily basis.

In some examples, mid-term prediction module 550 further receives, via communication circuitry 506, provider data for patient 14 from provider database 66. In some examples, the provider data stored by provider database 66 may include many different types of historical medical information about patient 14. For example, provider database 66 may store a medication history of the patient, a surgical procedure history of the patient, a hospitalization history of the patient, potassium levels of the patient over time, or one or more lab test results for the patient, etc.

Mid-term prediction module 550 applies the trained machine learning model to the parametric patient data and the provider data for patient 14 to perform mid-term monitoring of patient 14. In some examples, mid-term prediction module 550 performs the mid-term monitoring by generating a mid-term probability that a cardiac arrhythmia will occur in patient 14 within a mid-term time period (e.g., typically about 24 hours to about 48 hours). For example, mid-term prediction module 550 applies the trained machine learning model to the parametric patient data and the provider data for patient 14 to generate the mid-term probability that a cardiac arrhythmia will occur in patient 14 within the mid-term time period. For example, the machine learning model may convert the parametric patient data and the provider data into one or more vectors and tensors (e.g., multi-dimensional arrays) that represent the parametric patient data and the provider data. The machine learning model may apply mathematical operations to the one or more vectors and tensors to generate a mathematical representation of the parametric patient data and the provider data. The machine learning model may determine different weights that correspond to identified relationships between the parametric patient data and the provider data and the occurrence of cardiac arrhythmia within the mid-term time period. The machine learning model may apply the different weights to the parametric patient data and the provider data to generate the mid-term probability that a cardiac arrhythmia will occur in patient 14 within the mid-term time period. While in the foregoing example, the mid-term prediction module 550 applies the machine learning model to both parametric patient data and provider data for a plurality of patients, in some examples, the mid-term prediction module 550 applies the machine learning model to only parametric patient data and not provider data or to only provider data and not parametric patient data.

In some examples, mid-term prediction module 550 determines whether the determined mid-term probability that a cardiac arrhythmia will occur in patient 14 within a mid-term time period exceeds a predetermined threshold, e.g., set by a clinician. In response to determining that the mid-term probability exceeds the predetermined threshold, mid-term prediction module 550 transmits, via communication circuitry 506, instructions to IMD 16 causing IMD 16 to perform short-term monitoring of patient 14 as described above. In some examples, in response to determining that the mid-term probability exceeds the predetermined threshold, mid-term prediction module 550 may perform other actions, such as notifying, via output device 512, a clinician that the mid-term probability has exceeded the predetermined threshold or that mid-term prediction module 550 has determined that patient 14 is likely to suffer a cardiac arrhythmia within the mid-term time period.

In the foregoing example, mid-term prediction module 550 applies a machine-learning model to determine the mid-term probability that a cardiac arrhythmia will occur in patient 14 within a mid-term time period. In other examples, mid-term prediction module 550 may apply feature detection to parametric patient data to determine the mid-term probability that a cardiac arrhythmia will occur in patient 14 within a mid-term time period in a similar fashion as IMD 16 applies feature detection to parametric patient data to determine the short-term probability that a cardiac arrhythmia will occur in patient 14 within a short-term time period as described above.

As an example, mid-term prediction module 550 performs feature detection on parametric patient data, including electrocardiogram data. In this example, the parametric patient data includes one or more of an average frequency or an average amplitude of a T-wave of an electrocardiogram of patient 14. Mid-term prediction module 550 receives a raw electrocardiogram signal from IMD 16 or sensors 80 of FIG. 1, and extracts features from the raw electrocardiogram signal. In some examples, mid-term prediction module 550 identifies one or more of T-wave alternans, QRS morphology measures, etc. For example, mid-term prediction module 550 identifies one or more features of a T-wave of an electrocardiogram of patient 14 and applies a model to the one or more identified features to generate the mid-term probability that the cardiac arrhythmia will occur in patient 14 within the mid-term time period. In some examples, the one or more identified features are one or more amplitudes of the T-wave. In some examples, the one or more identified features are a frequency of the T-wave. In some examples, the one or more identified features include at least an amplitude of the T-wave and a frequency of the T-wave.

While IMD 16 may perform feature detection over a short-term time period due to battery and processing power constraints, external device 27 may not be so limited. For example, external device 27 may be easily charged, a larger battery, or have significantly more computing resources. Therefore, external device 27 may apply a feature detection algorithm that is more computationally-expensive, algorithmically complex, consumes more power, or analyzes parametric patient data over a longer period of time (e.g., a mid-term time period) than IMD 16.

Thus, the techniques disclosed herein may allow for enhanced patient care and increase the ability to prevent cardiac arrhythmias in a patient. For example, the knowledge that tachyarrhythmia has a relatively high likelihood of occurring within the next few days may be used to help guide preventative care for the patient. Furthermore, such a system as disclosed herein may offload complex cardiac arrhythmia prediction operations that are computationally-expensive and power consuming from medical devices where battery longevity is of critical concern, and activate short-term cardiac prediction operations on the medical device only when cardiac arrhythmia is predicted to have a relatively high likelihood of occurring within the next few days. Thus, the techniques of the disclosure may conserve power and extend battery life of a medical device by using the medical device for cardiac prediction only when a cardiac arrhythmia has a relatively high likelihood of occurring within a particular time span.

Figure 6:
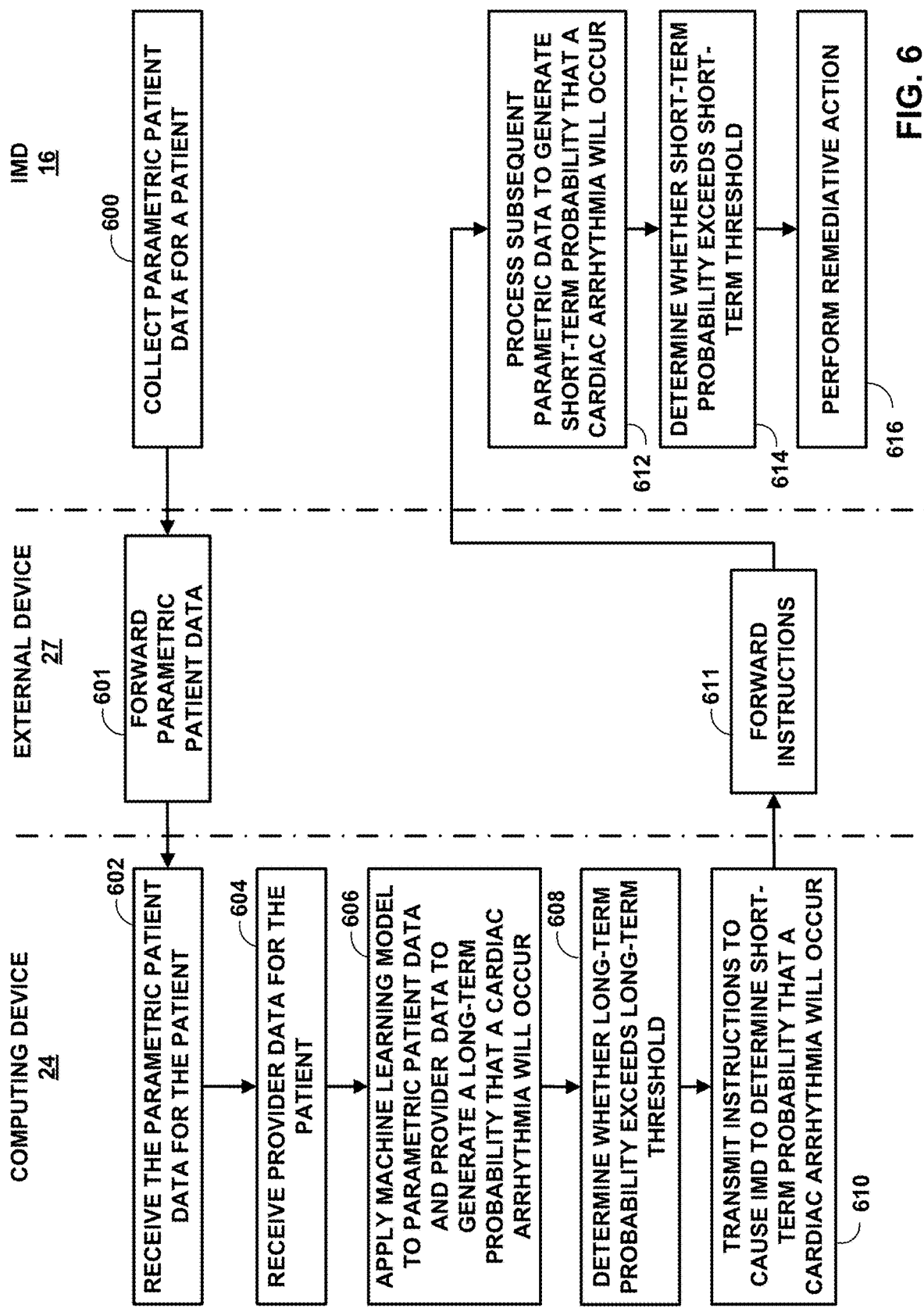
FIG. 6 is a flowchart illustrating an example operation in accordance with the techniques of the disclosure.

FIG. 6 is a flowchart illustrating an example operation in accordance with the techniques of the disclosure. For convenience, FIG. 6 is described with respect to FIG. 1. In some examples, the operation of FIG. 6 is an operation for providing multi-tier prediction of cardiac arrhythmia in patient 14, e.g., both long-term and short-term prediction of cardiac ventricular arrhythmias in patient 14.

In one example, IMD 16 collects parametric patient data for patient 114 (600). In some examples, the parametric patient data includes one or more of an activity level of the patient, a heart rate of the patient, a posture of the patient, a cardiac electrogram of the patient, a blood pressure of the patient, accelerometer data for the patient, or other types of parametric patient data. In some examples, the parametric patient data includes one or more values that represent average measurements of patient 14 over a long-term time period (e.g., about 24 hours to about 48 hours). In some examples, IMD 16 uploads the parametric patient data to external device 27. External device 27 forwards the parametric patient data to computing device 24 (601). In some examples, external device 27 collects additional parametric patient data, such as geographic location, accelerometer data, or input from patient 14. In some examples, external device 27 receives parametric patient data from other sources, such as one or more of sensors 80. External device 27 forwards the parametric patient data collected from each source to computing device 24. Computing device 24 receives, over network 25, the patent parametric data forwarded by external device 27 (602). In some examples, computing device 24 receives the parametric patient data on a daily basis.

Computing device 24 further receives provider data for patient 14 from provider database 66 (604). In some examples, the provider data stored by provider database 66 may include many different types of historical medical information about patient 14. For example, provider database 66 may store a medication history of the patient, a surgical procedure history of the patient, a hospitalization history of the patient, potassium levels of the patient over time, or one or more lab test results for the patient, etc.

Computing device 24 applies a machine learning model, trained using parametric patient data and provider data for a plurality of patients, to the parametric patient data and the provider data for patient 14 to generate a long-term probability that a cardiac arrhythmia will occur in patient 14 within a long-term time period (606). In some examples, the long-term time period is about 24 hours to about 48 hours. Computing device 24 determines whether the long-term probability exceeds a long-term predetermined threshold (608). In response to determining that the long-term probability exceeds the long-term predetermined threshold, computing device 24 transmits instructions causing IMD 16 to determine a short-term probability that the cardiac arrhythmia will occur in patient 14 within a short-term time period (610). In some examples, computing device 24 forwards the instructions to external device 27, which in turn forwards the instructions to IMD 16 (611). In some examples, the short-term time period is about 30 minutes to about 60 minutes). In some examples, in response to determining that the long-term probability exceeds the long-term predetermined threshold, computing device 24 may perform other actions, such as notifying a clinician that the long-term probability has exceeded the long-term predetermined threshold or that computing system 24 has determined that patient 14 is likely to suffer a cardiac arrhythmia within the long-term time period.

In response to receiving the instructions from computing device 24, IMD 16 processes subsequent parametric patient data to generate the short-term probability that the cardiac arrhythmia will occur in patient 14 within the short-term time period (612). In some examples, IMD 16 generates the short-term probability by performing feature detection on the subsequent parametric patient data. In some examples, IMD 16 may analyze similar parametric patient data to the parametric patient data analyzed by computing device 24 as described above. In other examples, IMD 16 analyzes parametric patient data that is different from the parametric patient data analyzed by computing device 24. For example, computing device 24 may analyze parametric patient data that represents one or more values that are averaged over a long-term period of time (e.g., about 24 hours to about 48 hours), while IMD 16 may analyze parametric patient data that represents one or more values that are averaged over a short-term period of time (e.g., about 30 minutes to about 60 minutes).

IMD 16 determines whether the short-term probability exceeds a short-term predetermined threshold (614). In response to determining that the short-term probability exceeds a short-term predetermined threshold, IMD 16 performs a remediative action to reduce the short-term probability that the cardiac arrhythmia will occur in patient 14 within the short-term time period (616). For example, IMD 16 may issue a notification of the short-term probability that the cardiac arrhythmia will occur in patient 14 within the short-term time period to computing device 24 such that patient 14 or a clinician may become aware of the likelihood the cardiac arrhythmia will occur in patient 14 within the short-term time period. As one example, the notification may instruct patient 14 to perform breathing exercises or take medicine to reduce the likelihood the cardiac arrhythmia will occur in patient 14 within the short-term time period. In another example, IMD 16 initiates therapy to patient 14, such as drug delivery therapy or electrical pacing therapy, to reduce the likelihood the cardiac arrhythmia will occur in patient 14 within the short-term time period.

Figure 7:
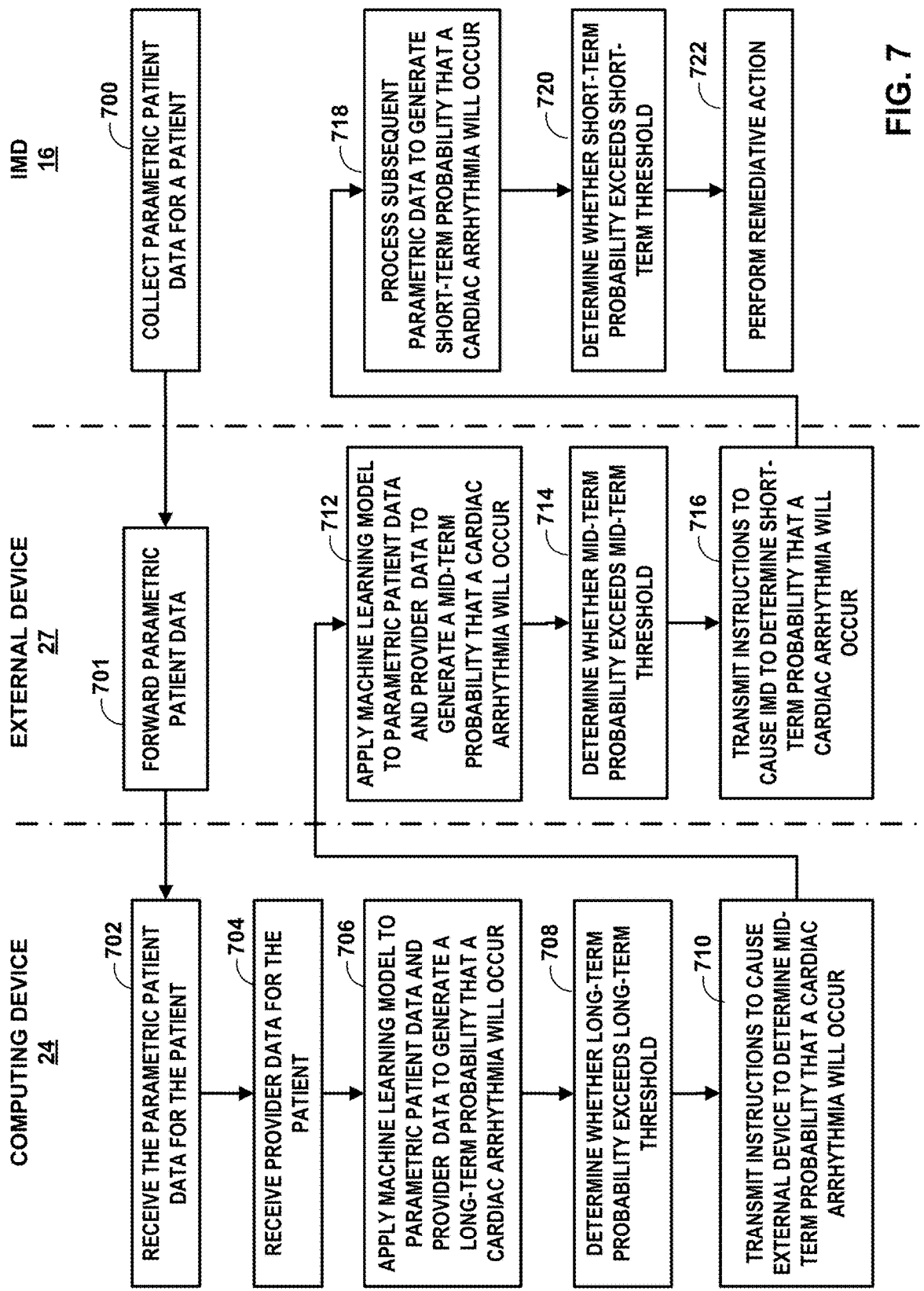
FIG. 7 is a flowchart illustrating an example operation in accordance with the techniques of the disclosure.

FIG. 7 is a flowchart illustrating an example operation in accordance with the techniques of the disclosure. For convenience, FIG. 7 is described with respect to FIG. 1. In some examples, the operation of FIG. 7 is an operation for providing multi-tier prediction of cardiac arrhythmia in patient 14, e.g., including long-term, mid-term, and short-term prediction of cardiac ventricular arrhythmias in patient 14. In the example of FIG. 7, long-term, mid-term, and short-term prediction of cardiac ventricular arrhythmias in patient 14 may correspond to predictions that cardiac ventricular arrhythmias in patient 14 is likely to occur in patient 14 over a long-term period of time (e.g., about 1 week or longer), a mid-term period of time (e.g., about 24 hours to about 48 hours), or a short-term period of time (e.g., about 30 minutes to about 60 minutes).

In one example, IMD 16 collects parametric patient data for patient 114 (700). In some examples, the parametric patient data includes one or more of an activity level of the patient, a heart rate of the patient, a posture of the patient, a cardiac electrogram of the patient, a blood pressure of the patient, accelerometer data for the patient, or other types of parametric patient data. In some examples, the parametric patient data includes one or more values that represent average measurements of patient 14 over a long-term time period (e.g., about 24 hours to about 48 hours). In some examples, IMD 16 uploads the parametric patient data to external device 501. External device 27 forwards the parametric patient data to computing device 24 (701). In some examples, external device 27 collects additional parametric patient data, such as geographic location, accelerometer data, input from patient 14. In some examples, external device 27 receives parametric patient data from other sources, such as one or more of sensors 80. External device 27 forwards the parametric patient data collected from each source to computing device 24. Computing device 24 receives, over network 25, the patent parametric data forwarded by external device 27 (702). In some examples, computing device 24 receives the parametric patient data on a daily basis.

Computing device 24 further receives provider data for patient 14 from provider database 66 (704). In some examples, the provider data stored by provider database 66 may include many different types of historical medical information about patient 14. For example, provider database 66 may store a medication history of the patient, a surgical procedure history of the patient, a hospitalization history of the patient, potassium levels of the patient over time, or one or more lab test results for the patient, etc.

Computing device 24 applies a machine learning model, trained using parametric patient data and provider data for a plurality of patients, to the parametric patient data and the provider data for patient 14 to generate a long-term probability that a cardiac arrhythmia will occur in patient 14 within a long-term time period (706). In some examples, the long-term time period is on the order of one week or longer.

Computing device 24 determines whether the long-term probability exceeds a long-term predetermined threshold (708).

In response to determining that the long-term probability exceeds the long-term predetermined threshold, computing device 24 transmits instructions causing external device 27 to determine a mid-term probability that the cardiac arrhythmia will occur in patient 14 within a mid-term time period (710). In some examples, in response to determining that the long-term probability exceeds the long-term predetermined threshold, computing device 24 may perform other actions, such as notifying a clinician that the long-term probability has exceeded the long-term predetermined threshold or that computing system 24 has determined that patient 14 is likely to suffer a cardiac arrhythmia within the long-term time period.

In response to receiving the instructions from computing device 24, external device 27 applies a machine learning model, trained using parametric patient data and provider data for a plurality of patients, to the parametric patient data and the provider data for patient 14 to generate a mid-term probability that a cardiac arrhythmia will occur in patient 14 within a mid-term time period (712). In some examples, external device 27 applies a machine learning model that is trained using parametric patient data and not provider data, to the parametric patient data and not the provider data for patient 14 to generate the mid-term probability that the cardiac arrhythmia will occur in patient 14 within a mid-term time period. In some examples, the mid-term time period is about 24 hours to about 48 hours. External device 27 determines whether the mid-term probability exceeds a mid-term predetermined threshold (714). In some examples, the mid-term predetermined threshold is 50%. In some examples, the mid-term predetermined threshold is another threshold, such as 75%, 80%, 90%, 99%, or 99.5%, or 99.9%.

In response to determining that the mid-term probability exceeds the mid-term predetermined threshold, external device 27 transmits instructions causing IMD 16 to determine a short-term probability that the cardiac arrhythmia will occur in patient 14 within a short-term time period (716). In some examples, the short-term time period is about 30 minutes to about 60 minutes). In some examples, in response to determining that the mid-term probability exceeds the mid-term predetermined threshold, external device 27 may perform other actions, such as notifying a clinician that the mid-term probability has exceeded the mid-term predetermined threshold or that external device 27 has determined that patient 14 is likely to suffer a cardiac arrhythmia within the mid-term time period.

In response to receiving the instructions from external device 27, IMD 16 processes subsequent parametric patient data to generate the short-term probability that the cardiac arrhythmia will occur in patient 14 within the short-term time period (718). In some examples, IMD 16 generates the short-term probability by performing feature detection on the subsequent parametric patient data. In some examples, IMD 16 may analyze similar parametric patient data to the parametric patient data analyzed by computing device 24 and/or external device 27 as described above. In other examples, IMD 16 analyzes parametric patient data that is different from the parametric patient data analyzed by computing device 24 and/or external device 27. For example, computing device 24 may analyze parametric patient data that represents one or more values that are averaged over a long-term period of time (e.g., about one week or greater), external device 27 may analyze parametric patient data that represents one or more values that are averaged over a mid-term period of time (e.g., about 24 hours to about 48 hours), while IMD 16 may analyze parametric patient data that represents one or more values that are averaged over a short-term period of time (e.g., about 30 minutes to about 60 minutes).

IMD 16 determines whether the short-term probability exceeds a short-term predetermined threshold (720). In response to determining that the short-term probability exceeds a short-term predetermined threshold, IMD 16 performs a remediative action to reduce the short-term probability that the cardiac arrhythmia will occur in patient 14 within the short-term time period (722). For example, IMD 16 may issue a notification of the short-term probability that the cardiac arrhythmia will occur in patient 14 within the short-term time period to computing device 24 such that patient 14 or a clinician may become aware of the likelihood the cardiac arrhythmia will occur in patient 14 within the short-term time period. In another example, IMD 16 initiates therapy to patient 14, such as drug delivery therapy or electrical pacing therapy, to reduce the likelihood the cardiac arrhythmia will occur in patient 14 within the short-term time period.

As described herein, the use of the terms "long-term probability," "mid-term probability," and "short-term probability," as well as the use of the terms "long-term probability threshold," "mid-term probability threshold," and "short-term probability threshold," are used throughout the disclosure solely to differentiate the terms from one another. These terms are not limited to any particular length of time. For example, the term "long-term probability" is interchangeable with the term "first probability," the term "mid-term probability" is interchangeable with the term "second probability," the term "short-term probability" is interchangeable with the term "third probability," the term "long-term probability threshold" is interchangeable with the term "first probability threshold," the term "mid-term probability threshold" is interchangeable with the term "second probability threshold," and the term "short-term probability threshold" is interchangeable with the term "third probability threshold."

Figure 8A:
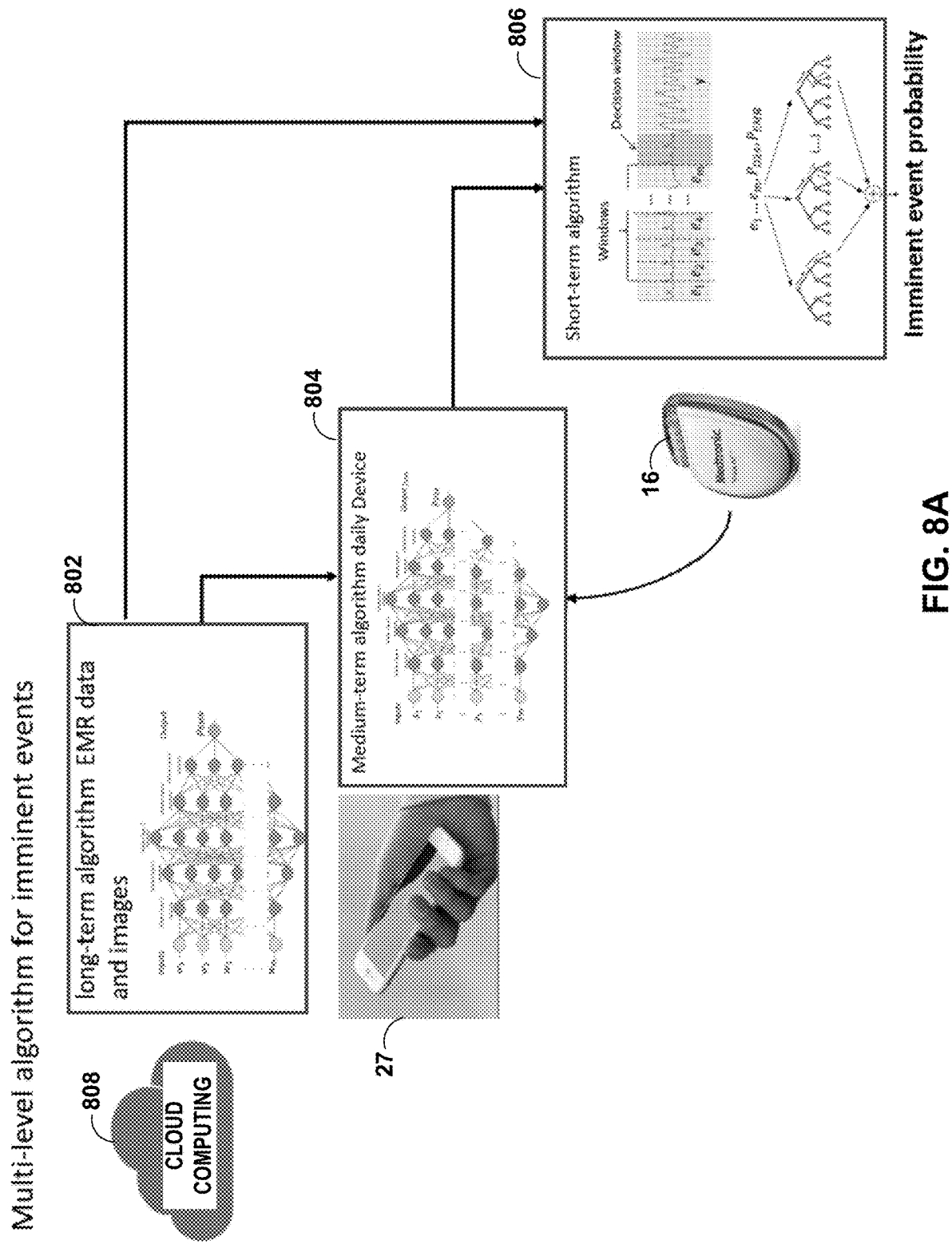
FIG. 8A is a flowchart illustrating an example operation in accordance with the techniques of the disclosure.

FIG. 8A is a flowchart illustrating an example operation in accordance with the techniques of the disclosure. Specifically, the flowchart of FIG. 8A depicts an operation for providing multi-tier prediction of cardiac arrhythmia in patient 14, e.g., including long-term, mid-term, and short-term of cardiac ventricular arrhythmias in patient 14. For convenience, FIG. 8 is described with respect to FIG. 1.

As depicted in the example of FIG. 8, cloud computing network 808 applies long-term algorithm 802 to provider data for patient 14 to generate a long-term probability that cardiac arrhythmia will occur in patient 14 over a long-term time period. Additional detail of long-term algorithm 802 is depicted in FIG. 8B. In some examples, cloud computing network 808 comprises one or more computing devices 24 of FIG. 1.

In response to determining that a long-term probability that patient 14 will experience cardiac arrythmia exceeds a long-term predetermined threshold, cloud computing network 808 transmits instructions causing external device 27 to apply mid-term algorithm 804 to parametric patient data for patient 14 to generate a mid-term probability that cardiac arrhythmia will occur in patient 14 over a mid-term time period. As illustrated in FIG. 8A, external device 27 may receive parametric data from IMD 16, e.g., on a daily or other periodic basis. Additional detail of mid-term algorithm 804 is depicted in FIG. 8C.

In response to determining that a mid-term probability that patient 14 will experience cardiac arrythmia exceeds a mid-term predetermined threshold, external device 27 transmits instructions causing IMD 16 to apply short-term algorithm 806 to parametric patient data for patient 14 to generate a short-term probability that cardiac arrhythmia will occur in patient 14 over a short-term time period. Additional detail of short-term algorithm 806 is depicted in FIG. 8D.

In some examples, each higher-level algorithm may supply a risk factor to a lower-level algorithm, which the lower-level algorithm may include in its determination of a probability that cardiac arrhythmia will occur in patient 14. For example, mid-term algorithm 804 may use the long-term probability that cardiac arrhythmia will occur in patient 14 over a long-term time period, generated by long-term algorithm 802, in the determination of the mid-term probability that cardiac arrhythmia will occur in patient 14 over a mid-term time period. Similarly, short-term algorithm 806 may use the mid-term probability that cardiac arrhythmia will occur in patient 14 over a mid-term time period, generated by mid-term algorithm 804, in the determination of the short-term probability that cardiac arrhythmia will occur in patient 14 over a short-term time period.

The use of the multiple levels of cardiac arrythmia prediction depicted in FIG. 8A may extend the battery life of IMD 16, thereby allowing IMD 16 to be implanted in patient 14 for longer periods of time without replacement. Furthermore, the use of such multiple levels of cardiac arrythmia prediction may provide a high degree of sensitivity, specificity, and accuracy to the needs and risks of patient 14.

Figure 8B:
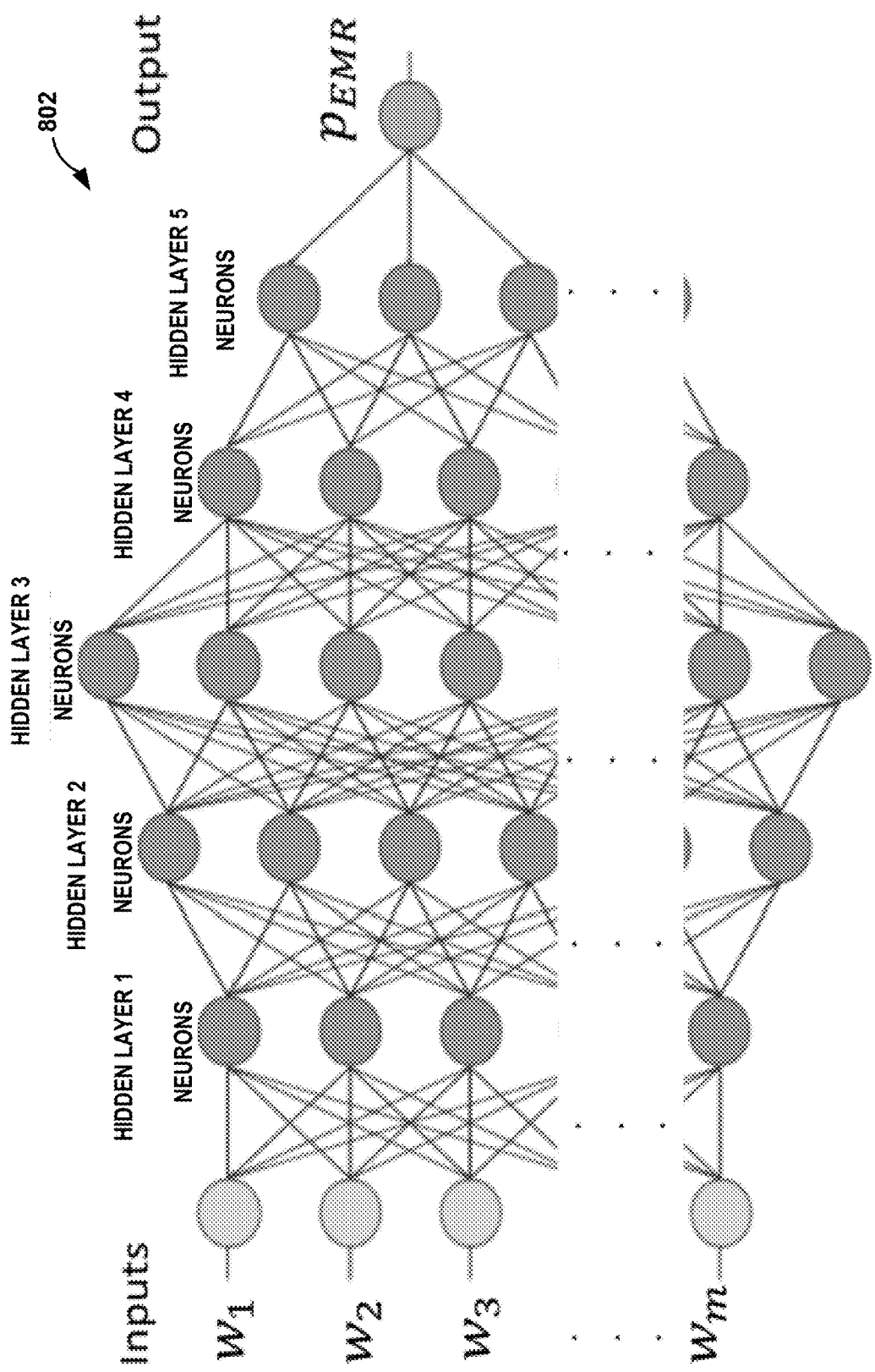
FIG. 8B is a block diagram illustrating the algorithm for long-term prediction of cardiac arrythmia depicted in the example of FIG. 8A in further detail.
Figure 8C:
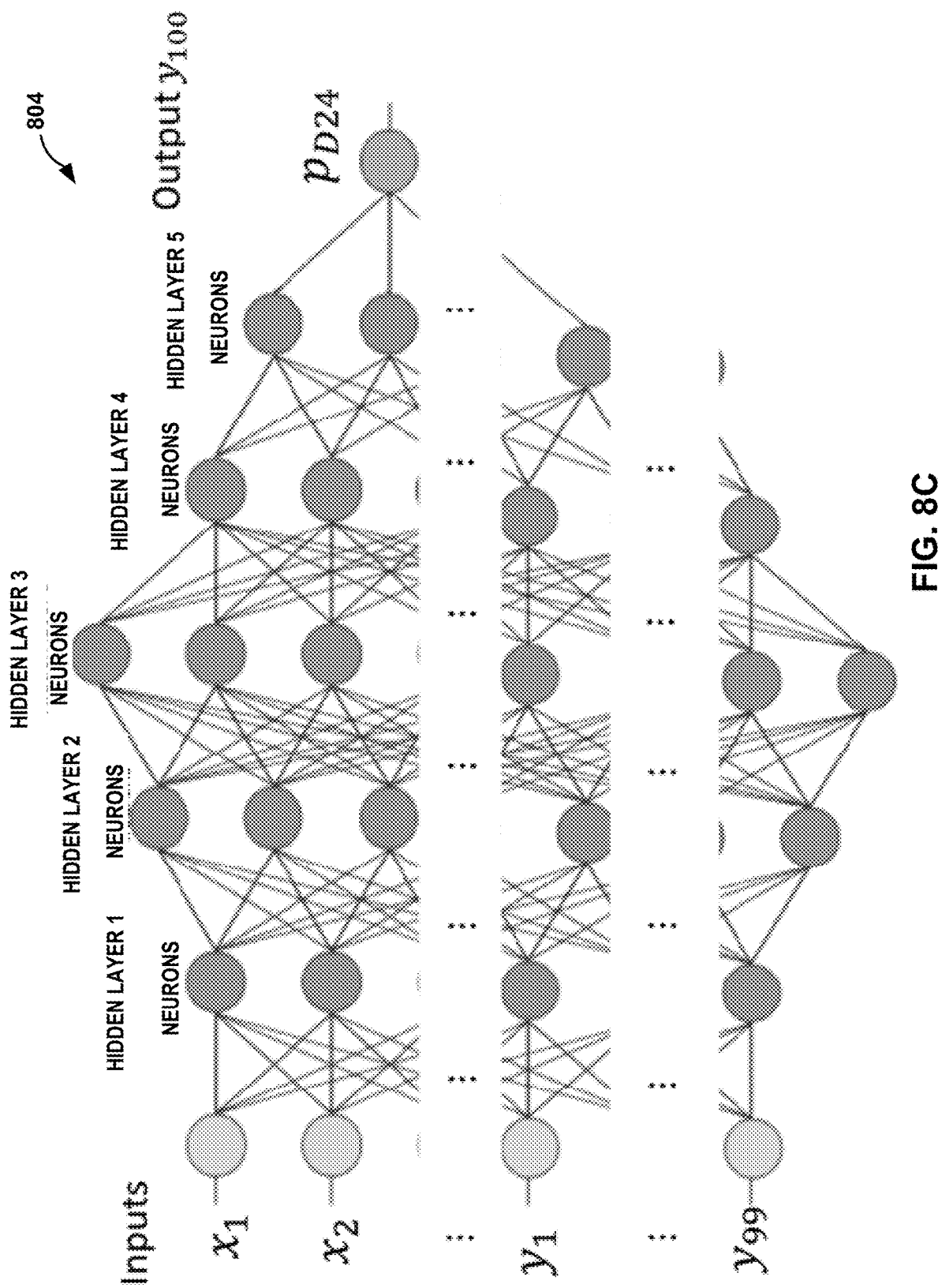
FIG. 8C is a block diagram illustrating the algorithm for mid-term prediction of cardiac arrythmia depicted in the example of FIG. 8A in further detail.
Figure 8D:
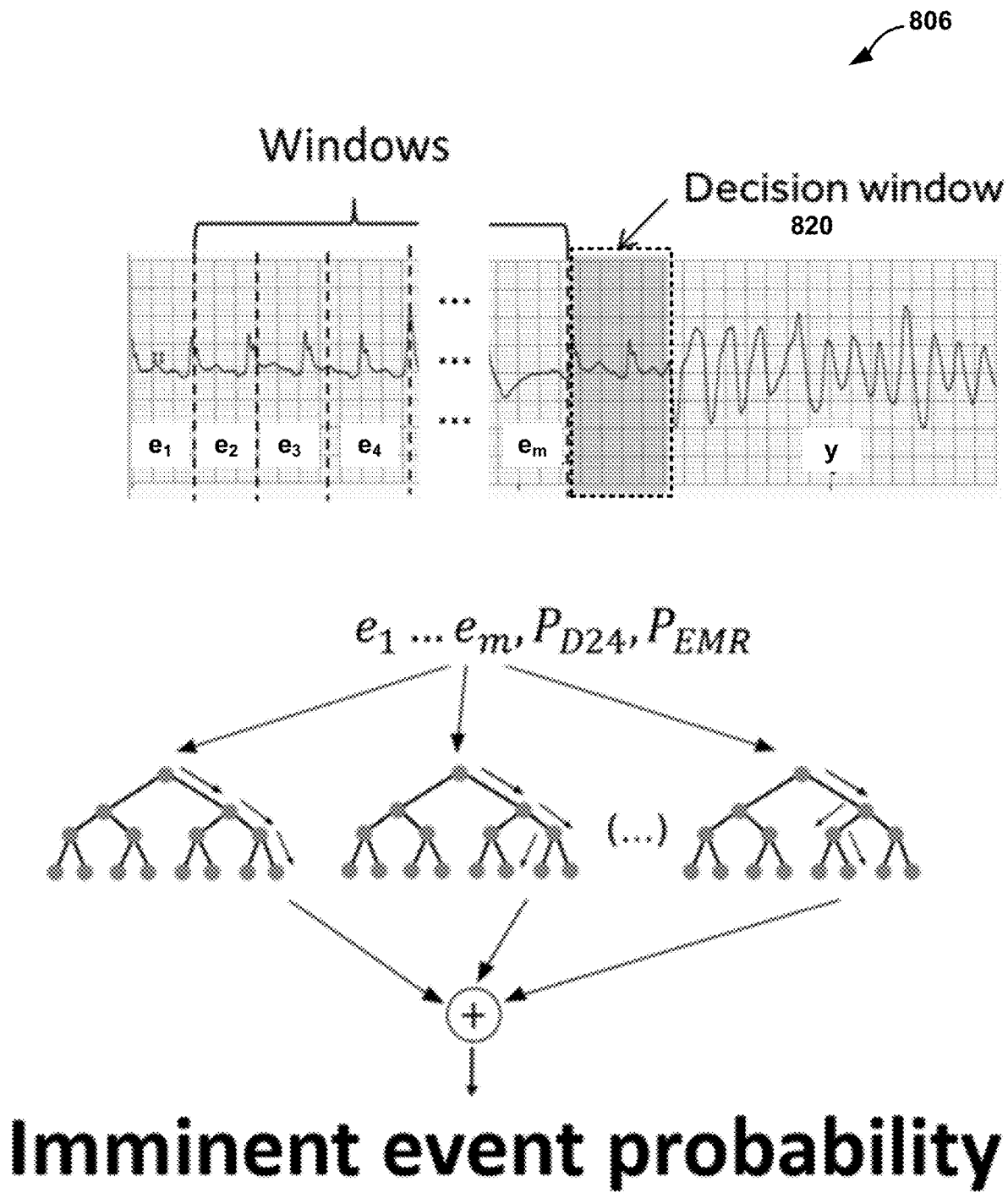
FIG. 8D is a block diagram illustrating the algorithm for short-term prediction of cardiac arrythmia depicted in the example of FIG. 8A in further detail.

FIG. 8B is a block diagram illustrating algorithm 802 for long-term prediction of cardiac arrythmia depicted in the example of FIG. 8A in further detail. In the example of FIG. 8B, one or more computing devices 24 of cloud computing network 808 applies a plurality of types of provider data and parametric patient data $w_1, w_2, w_3, \ldots w_m$, to layers of a neural network comprising a plurality of neurons and a plurality of hidden layers 1-5. In some examples, each of $w_1, w_2, w_3, \ldots w_m$ correspond to a different type of provider data or parametric patient data, such as a medication history of the patient, a surgical procedure history of patient 14, an electrocardiogram of patient 14, etc. The neural network processes provider data and parametric patient data $w_1, w_2, w_3, \ldots w_m$ by mapping the inputs across the plurality of neurons and plurality of hidden layers 1-5 to generate an output $P_{EMR}$, which is a long-term probability that a cardiac arrythmia will occur in patient 14 over a long-term time period.

FIG. 8C is a block diagram illustrating algorithm 804 for mid-term prediction of cardiac arrythmia depicted in the example of FIG. 8A in further detail. In the example of FIG. 8B, external device 27 applies a plurality of types of provider data and parametric patient data $x_1, x_2, x_3, \ldots x_m$, to layers of a neural network comprising a plurality of neurons and a plurality of hidden layers 1-5. In some examples, each of $x_1, x_2, x_3, \ldots x_m$ correspond to a different type of provider data or parametric patient data, such as a medication history of the patient, a surgical procedure history of patient 14, an electrocardiogram of patient 14, etc. The neural network processes provider data and parametric patient data $x_1, x_2, x_3, \ldots x_m$ by mapping the inputs across the plurality of neurons and plurality of hidden layers 1-5 to generate an output $P_{D24}$, which is a mid-term probability that a cardiac arrythmia will occur in patient 14 over a mid-term time period.

FIG. 8D is a block diagram illustrating algorithm 806 for short-term prediction of cardiac arrythmia depicted in the example of FIG. 8A in further detail. As depicted in FIG. 8D, IMD 16 generates a short-term probability that a cardiac arrythmia will occur in patient 14 by performing feature detection on each of a plurality of windows $e_1, e_2, e_3, e_4, \ldots e_m$ of the parametric patient data. Each of windows $e_1, e_2, e_3, e_4, \ldots e_m$ represents a segment of time during which IMD 16 applies criteria to determine if one or more indicators of subsequent cardiac arrythmia are present. As depicted in the example of FIG. 8D, at decision window 820, IMD 16 determines a probability that that a cardiac arrythmia will likely occur in patient 14 during the short-term time period. Additional information regarding the use of multiple parameters to predict cardiac arrythmia may be found, e.g., in U.S. Patent App. Pub. No. 2017/0354365 to Zhou et al., entitled "MULTI-PARAMETER PREDICTION OF ACUTE CARDIAC EPISODES AND ATTACKS," filed on Jun. 12, 2017, and published on Dec. 14, 2017, the entire content of which is incorporated herein by reference.

In some examples, IMD 16 may use the feature detection of the parametric patient data in conjunction with the long-term probability $P_{EMR}$ generated by one or more computing devices 24 that a cardiac arrythmia will occur in patient 14 over a long-term time period and the mid-term probability $P_{D24}$ generated by external device 27 that a cardiac arrythmia will occur in patient 14 over a mid-term time period to determine the probability that a cardiac arrythmia will likely occur in patient 14 during the short-term time period. In some examples, IMD 16 applies different weights to each of the feature detection, the long-term probability $P_{EMR}$, and the mid-term probability $P_{D24}$, to determine the probability that a cardiac arrythmia will likely occur in patient 14 during the short-term time period. In some examples, IMD 16 applies a decision tree to each of the feature detection, the long-term probability $P_{EMR}$, and the mid-term probability $P_{D24}$, to determine the probability that a cardiac arrythmia will likely occur in patient 14 during the short-term time period.

Figure 9:
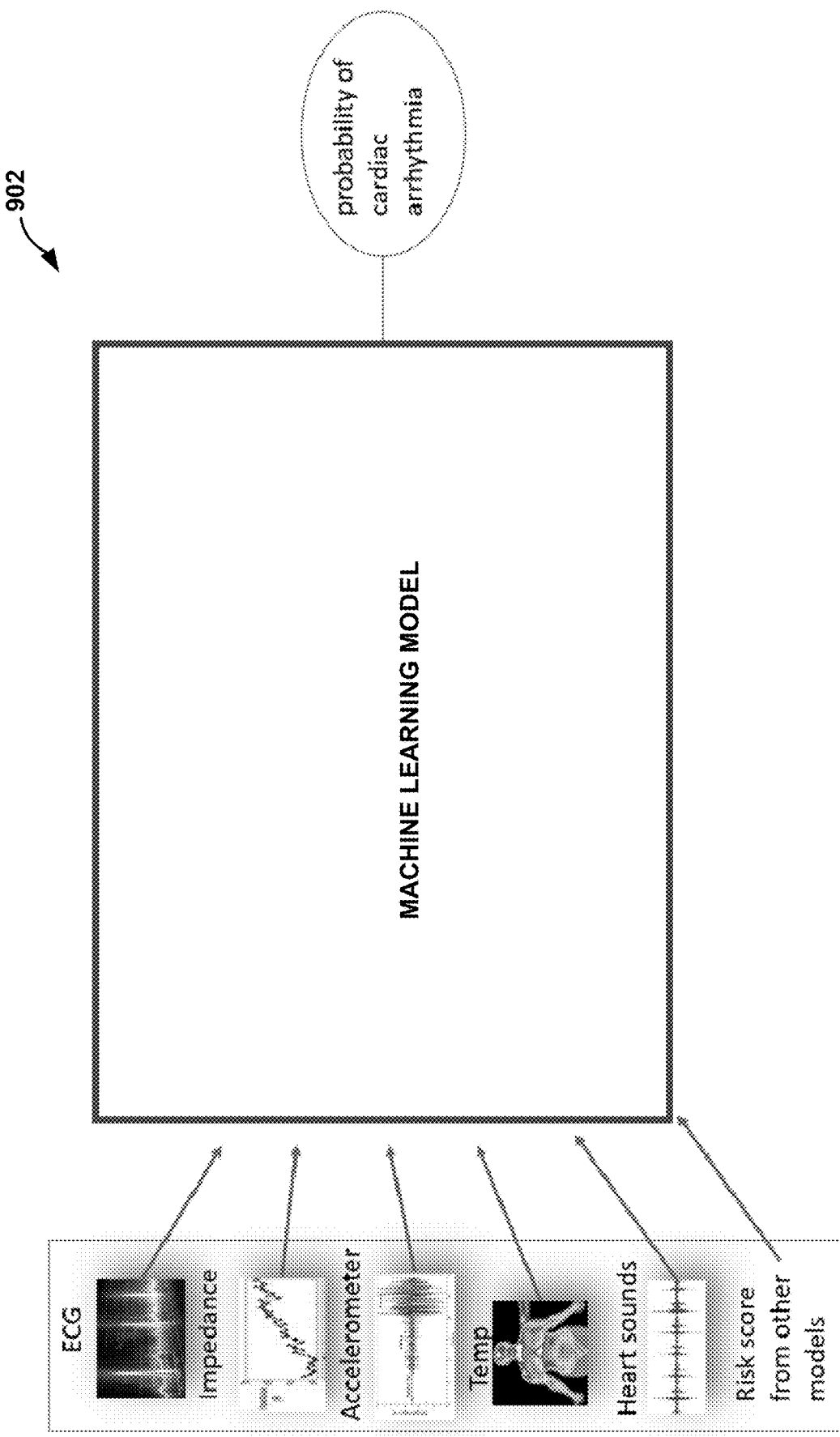
FIG. 9 is a block diagram illustrating an example algorithm for short-term prediction of cardiac arrythmia in accordance with the techniques of the disclosure.

FIG. 9 is a block diagram illustrating an example algorithm 902 for short-term prediction of cardiac arrythmia in accordance with the techniques of the disclosure. For convenience, FIG. 9 is described with respect to FIG. 1. In some examples, example algorithm 902 operates in a substantially similar fashion to algorithm 806 for short-term prediction of cardiac arrythmia of FIGS. 8A and 8D. In some examples, IMD 16 may process parametric patient data of multiple types to determine the short-term probability that a cardiac arrythmia will likely occur in patient 14 during the short-term time period. In the example of FIG. 9, IMD 16 applies a machine learning model to calculate the short-term probability that a cardiac arrythmia will likely occur in patient 14 during the short-term time period. For example, as inputs, the machine learning model of IMD 16 may receive perform feature detection on different types of parametric patient data. For example, IMD may perform feature detection on one or more of electrocardiogram data, electrode impedance measurements, accelerometer data, temperature data for patient 14, audio data of a heart of patient 14, or risk scores computed by other algorithms of different levels. Such risk scores may include, e.g., the long-term probability $P_{EMR}$ generated by one or more computing devices 24 that a cardiac arrythmia will occur in patient 14 over a long-term time period and the mid-term probability $P_{D24}$ generated by external device 27 that a cardiac arrythmia will occur in patient 14 over a mid-term time period.

Thus, the techniques disclosed herein may allow for enhanced patient care and increase the ability to prevent cardiac arrhythmias in a patient. For example, the knowledge that tachyarrhythmia has a relatively high likelihood of occurring within the next few days may be used to help guide preventative care for the patient. Further, the knowledge that tachyarrhythmia has a relatively high likelihood of occurring within the next few minutes or hours may be used to guide preventative therapies or emergency care for the patient. Furthermore, such a system as disclosed herein may move long-term cardiac arrhythmia prediction operations that are computationally-expensive and power consuming from a personal medical device of a patient to a cloud computing system, and activate short-term cardiac prediction operations on the medical device only when the cloud computing system predicts that a cardiac arrhythmia has a relatively high likelihood of occurring within the next few days. Thus, the techniques of the disclosure may conserve power and extend battery life of a medical device by using the medical device for cardiac prediction only when a cardiac arrhythmia has a relatively high likelihood of occurring within a particular time span.

In some examples, the techniques of the disclosure include a system that comprises means to perform any method described herein. In some examples, the techniques of the disclosure include a computer-readable medium comprising instructions that cause processing circuitry to perform any method described herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

Various examples have been described. These and other examples are within the scope of the following claims.

What is claimed is:

1. A system comprising:
an implantable medical device (IMD) comprising IMD processing circuitry, a storage medium, and one or more electrodes, wherein the IMD is configured to collect parametric data for the patient, and the parametric data comprises data determined from a cardiac electrogram sensed via the one or more electrodes; and
a computing device comprising processing circuitry and a storage medium, the computing device configured to:
receive the parametric patient data for the patient from the IMD;
apply a machine learning model, trained using parametric patient data for a plurality of patients, to the parametric patient data to generate a first probability that a cardiac arrhythmia will occur in the patient within a first time period;
determine that the first probability exceeds a predetermined threshold; and
in response to the determination that the first probability exceeds the predetermined threshold, transmit instructions to the IMD causing the IMD to determine a second probability that the cardiac arrhythmia will occur in the patient within a second time period, and
wherein the IMD is configured to:
determine the second probability that the cardiac arrhythmia will occur in the patient within the second time period based on the parametric data in response to the instructions, and
in response to the determination that the second probability is greater than a second probability threshold, perform at least one of the following:
output an indication of a likelihood the patient is to suffer the cardiac arrhythmia within the second time period, or
perform a remediative action to reduce the second probability that the cardiac arrhythmia will occur in the patient within the second time period.

2. The system of claim 1, wherein the computing device is further configured to receive provider data for the patient, wherein to apply the machine learning model, the computing device is configured to apply a machine learning model, trained using parametric patient data and provider data for a plurality of patients, to the parametric patient data and the provider data for the patient to generate the first probability that the cardiac arrhythmia will occur in the patient within the first time period.

3. The system of claim 1, wherein the parametric patient data includes at least one of:
physiological data for the patient;
an age of the patient;
a gender of the patient;
activity patterns of the patient;
sleep patterns of the patient;
gait changes of the patient;
device-related data for the IMD;
temperature trends of the patient; or
temperature trends of the IMD.

4. The system of claim 3, wherein the device-related data for the IMD includes at least one of:
an impedance of one or more electrodes of the IMD;
a selection of electrodes;
a drug delivery schedule for the IMD;

a history of electrical pacing therapy delivered to the patient;
diagnostic data for the IMD;
a detected activity level of the patient;
a detected posture of the patient;
a detected temperature of the patient; or
a detected sleep state of the patient.

5. The system of claim 2, wherein the provider data for the patient includes at least one of:
a medication history of the patient;
a surgical procedure history of the patient;
a hospitalization history of the patient;
a potassium level of the patient; or
one or more lab test results for the patient.

6. The system of claim 1, wherein the first time period is greater than 1 day and the second time period is less than 1 day.

7. The system of claim 1, wherein the computing device is further configured to:
after transmitting the instructions to the IMD receive, from the at least one of the IMD, feedback indicating whether the cardiac arrhythmia occurred in the patient within the first time period; and
update the machine learning model with the feedback indicating whether the cardiac arrhythmia occurred in the patient within the first time period.

8. A system comprising:
a medical device comprising medical device processing circuitry, a storage medium, and one or more electrodes, wherein the medical device is configured to collect parametric data for the patient, and the parametric data comprises data determined from a cardiac electrogram sensed via the one or more electrodes; and
an external device configured to:
receive instructions to generate a first probability that a cardiac arrhythmia will occur in the patient within a first time period;
in response to the instructions, process the parametric patient data to generate the first probability that the cardiac arrhythmia will occur in the patient within the first time period;
determine that the first probability exceeds a first predetermined threshold;
in response to the determination that the first probability exceeds the first predetermined threshold, transmit instructions to the medical device causing the medical device to determine a second probability that the cardiac arrhythmia will occur in the patient within a second time period, and
wherein the medical device is configured to:
determine the second probability that the cardiac arrhythmia will occur in the patient within the second time period based on the parametric data in response to the instructions, and
in response to the determination that the second probability is greater than a second probability threshold, perform at least one of the following:
output an indication of a likelihood the patient is to suffer the cardiac arrhythmia within the second time period, or
perform a remediative action to reduce the second probability that the cardiac arrhythmia will occur in the patient within the second time period.

9. The system of claim 8, wherein to process the parametric patient data to generate the first probability that the cardiac arrhythmia will occur in the patient within the first time period, the external device is configured to apply a machine learning model, trained using parametric patient data for a plurality of patients, to the parametric patient data to generate the first probability that the cardiac arrhythmia will occur in the patient within the first time period.

10. The system of claim 8, wherein to process the parametric patient data to generate the first probability that the cardiac arrhythmia will occur in the patient within the first time period, the external device is configured to perform feature detection of the parametric patient data to generate the first probability that the cardiac arrhythmia will occur in the patient within the first time period.

11. The system of claim 8, wherein the external device is further configured to:
receive, from at least one of the medical device or one or more sensors, the parametric patient data; and
transmit, to a computing device, the received parametric patient data.

12. The system of claim 11, wherein the external device is further configured to:
determine a geographic location of the patient; and
transmit the determined geographic location with the parametric patient data to the computing device.

13. The system of claim 8, wherein the external device comprises at least one of a mobile device or a wearable electronic device.

14. A method comprising:
receiving, by a computing device comprising processing circuitry and a storage medium, parametric patient data for a patient;
applying, by the computing device, a machine learning model, trained using parametric patient data for a plurality of patients, to the parametric patient data to generate a first probability that a cardiac arrhythmia will occur in the patient within a first time period;
determining, by the computing device, that the first probability exceeds a predetermined threshold;
in response to the determination that the first probability exceeds the predetermined threshold, transmitting, by the computing device, instructions to an implantable medical device (IMD) causing the IMD to determine a second probability that the cardiac arrhythmia will occur in the patient within a second time period;
determining, by the IMD, the second probability that the cardiac arrhythmia will occur in the patient within the second time period based on the parametric data in response to the instructions; and
in response to the determination that the second probability is greater than a second probability threshold, performing, by the IMD, at least one of the following:
outputting an indication of a likelihood the patient is to suffer the cardiac arrhythmia within the second time period, or
performing a remediative action to reduce the second probability that the cardiac arrhythmia will occur in the patient within the second time period.

15. The method of claim 14, further comprising receiving, by the computing device, provider data for the patient,
wherein applying the machine learning model comprises applying a machine learning model, trained using parametric patient data and provider data for a plurality of patients, to the parametric patient data and the provider data for the patient to generate the first probability that the cardiac arrhythmia will occur in the patient within the first time period.

16. The method of claim 14, further comprising:
after transmitting the instructions to the IMD, receiving, by the computing device and from the IMD, feedback indicating whether the cardiac arrhythmia occurred in the patient within the first time period; and updating, by the computing device, the machine learning model with the feedback indicating whether the cardiac arrhythmia occurred in the patient within the first time period.

17. The system of claim 1, the system further comprising:

an external device configured to:

receive instructions, from the computing device, to generate a mid-term probability that the cardiac arrhythmia will occur in the patient within a mid-term time period;

in response to the instructions, process the parametric patient data to generate the mid-term probability that the cardiac arrhythmia will occur in the patient within the mid-term time period;

determine that the mid-term probability exceeds a mid-term predetermined threshold; and in response to the determination that the mid-term probability exceeds the mid-term predetermined threshold, transmit instructions to the IMD causing the IMD to determine the second probability that the cardiac arrhythmia will occur in the patient within the second time period.

* * * * *